United States Patent
Gamache et al.

(10) Patent No.: US 10,369,015 B2
(45) Date of Patent: Aug. 6, 2019

(54) IMPLANT INSERTER HAVING A LATERALLY-EXTENDING DOVETAIL ENGAGEMENT FEATURE

(75) Inventors: Thomas Gamache, Westport, MA (US); Michael D. Sorrenti, Middleboro, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/364,280

(22) Filed: Feb. 1, 2012

(65) Prior Publication Data

US 2012/0150301 A1   Jun. 14, 2012

Related U.S. Application Data

(63) Continuation-in-part of application No. 13/237,200, filed on Sep. 20, 2011, which is a continuation-in-part
(Continued)

(51) Int. Cl.
| | |
|---|---|
| *A61B 17/16* | (2006.01) |
| *A61F 2/46* | (2006.01) |
| *A61B 17/80* | (2006.01) |
| *A61B 17/88* | (2006.01) |
| *A61F 2/44* | (2006.01) |

(Continued)

(52) U.S. Cl.
CPC ........ *A61F 2/4611* (2013.01); *A61B 17/1631* (2013.01); *A61B 17/808* (2013.01); *A61B 17/8875* (2013.01); *A61F 2/447* (2013.01); *A61B 17/1757* (2013.01); *A61B 17/80* (2013.01); *A61B 2017/0256* (2013.01); *A61F 2002/30387* (2013.01); *A61F 2002/30578* (2013.01); *A61F 2002/30823* (2013.01); *A61F 2002/30904* (2013.01); *A61F 2002/4475* (2013.01); *A61F 2002/4627* (2013.01); *A61F 2002/4629* (2013.01); *A61F 2002/4687* (2013.01)

(58) Field of Classification Search
CPC .............. A61B 17/8875; A61B 17/808; A61B 17/1631
USPC ........................................... 606/99; 81/177.6
See application file for complete search history.

(56) References Cited

U.S. PATENT DOCUMENTS

| | | | |
|---|---|---|---|
| 1,636,636 | A | 12/1926 | Humble |
| 1,677,337 | A | 7/1928 | Grove |

(Continued)

FOREIGN PATENT DOCUMENTS

| | | |
|---|---|---|
| CN | 201244104 | 5/2009 |
| CN | 101631516 | 1/2010 |

(Continued)

OTHER PUBLICATIONS

Non-published U.S. Appl. No. 13/364,280, filed Feb. 1, 2012.
(Continued)

*Primary Examiner* — Olivia C Chang

(57) ABSTRACT

A spinal implant inserter having a) an outer sleeve having a bore, and b) a forked inner shaft having a proximal rod and a pair of distal tynes extending therefrom, each distal tyne comprising an engagement feature having a laterally-extending dovetail feature. An assembly comprising the implant inserter and an implant having a pair of mating dovetail features.

3 Claims, 16 Drawing Sheets

Related U.S. Application Data of application No. 13/237,233, filed on Sep. 20, 2011, which is a continuation-in-part of application No. 13/237,174, filed on Sep. 20, 2011.

(60) Provisional application No. 61/466,309, filed on Mar. 22, 2011, provisional application No. 61/385,959, filed on Sep. 23, 2010, provisional application No. 61/466,321, filed on Mar. 22, 2011.

(51) Int. Cl.
  A61B 17/17 (2006.01)
  A61B 17/02 (2006.01)
  A61F 2/30 (2006.01)

(56) References Cited

U.S. PATENT DOCUMENTS

| | | |
|---|---|---|
| 2,304,703 A | 12/1942 | O'Leary |
| 4,105,034 A | 8/1978 | Shalaby |
| 4,130,639 A | 12/1978 | Shalaby |
| 4,140,678 A | 2/1979 | Shalaby |
| 4,141,087 A | 2/1979 | Shalaby |
| 4,205,399 A | 6/1980 | Shalaby |
| 4,208,511 A | 6/1980 | Shalaby |
| 4,349,921 A | 9/1982 | Kuntz |
| 4,743,256 A | 5/1988 | Brantigan |
| 4,863,476 A | 9/1989 | Shepperd |
| 4,904,261 A | 2/1990 | Dove et al. |
| 4,955,908 A | 9/1990 | Frey |
| 5,041,113 A | 8/1991 | Biedermann |
| 5,059,193 A | 10/1991 | Kuslich |
| 5,123,926 A | 6/1992 | Pisharodi |
| 5,147,361 A | 9/1992 | Ojima et al. |
| 5,209,751 A | 5/1993 | Farris |
| 5,290,312 A | 3/1994 | Kojimoto et al. |
| 5,306,308 A | 4/1994 | Gross |
| 5,344,252 A | 9/1994 | Kakimoto |
| 5,352,231 A | 10/1994 | Brumfield |
| 5,370,697 A | 12/1994 | Baumgartner |
| 5,390,683 A | 2/1995 | Pishardi |
| 5,391,170 A | 2/1995 | McGuire |
| 5,395,372 A | 3/1995 | Holt |
| 5,397,364 A | 3/1995 | Kozak |
| 5,443,514 A | 8/1995 | Steffee |
| 5,443,515 A | 8/1995 | Cohen |
| 5,464,407 A * | 11/1995 | McGuire ............ 606/86 R |
| 5,464,929 A | 11/1995 | Bezwada |
| 5,499,986 A | 3/1996 | Dimarco |
| 5,522,899 A | 6/1996 | Michelson |
| 5,529,580 A * | 6/1996 | Kusunoki et al. ........ 606/170 |
| 5,534,029 A | 7/1996 | Shima |
| 5,534,031 A | 7/1996 | Matsuzaki |
| 5,554,191 A | 9/1996 | Lahille et al. |
| D374,287 S | 10/1996 | Goble |
| 5,578,034 A | 11/1996 | Estes |
| 5,591,166 A | 1/1997 | Bernhardt et al. |
| 5,595,751 A | 1/1997 | Bezwada |
| 5,597,579 A | 1/1997 | Bezwada |
| 5,601,553 A | 2/1997 | Trebing et al. |
| 5,607,687 A | 3/1997 | Bezwada |
| 5,609,635 A | 3/1997 | Michelson |
| 5,609,636 A | 3/1997 | Kohrs et al. |
| 5,618,552 A | 4/1997 | Bezwada |
| 5,620,458 A | 4/1997 | Green et al. |
| 5,620,698 A | 4/1997 | Bezwada |
| 5,645,598 A | 7/1997 | Brosnahan, III |
| 5,645,850 A | 7/1997 | Bezwada |
| 5,648,088 A | 7/1997 | Bezwada |
| 5,653,763 A | 8/1997 | Errico |
| 5,658,335 A | 8/1997 | Allen |
| 5,662,655 A | 9/1997 | Laboureau |
| 5,665,122 A | 9/1997 | Kambin |
| 5,676,666 A | 10/1997 | Oxland |
| 5,697,977 A | 12/1997 | Pisharodi |
| 5,698,213 A | 12/1997 | Jamiolkowski |
| 5,700,583 A | 12/1997 | Jamiolkowski |
| 5,713,899 A | 2/1998 | Marnay |
| 5,716,415 A | 2/1998 | Steffee |
| 5,755,796 A | 5/1998 | Ibo et al. |
| 5,772,661 A | 6/1998 | Michelson |
| 5,776,196 A | 7/1998 | Matsuzaki |
| 5,779,707 A | 7/1998 | Bertholet |
| 5,782,832 A | 7/1998 | Larsen et al. |
| 5,785,713 A | 7/1998 | Jobe |
| 5,788,698 A | 8/1998 | Savornin |
| 5,797,912 A | 8/1998 | Runciman |
| 5,797,918 A | 8/1998 | McGuire |
| 5,800,435 A | 9/1998 | Errico et al. |
| 5,800,440 A | 9/1998 | Stead |
| 5,859,150 A | 1/1999 | Jamiolkowski |
| 5,860,973 A | 1/1999 | Michelson |
| 5,865,848 A | 2/1999 | Baker |
| 5,888,223 A | 3/1999 | Bray, Jr. |
| 5,888,224 A | 3/1999 | Beckers et al. |
| 5,893,889 A | 4/1999 | Harrington |
| 5,893,890 A | 4/1999 | Pisharodi |
| 5,904,689 A | 5/1999 | Jonjic |
| 5,913,860 A | 6/1999 | Scholl |
| 5,980,522 A | 11/1999 | Koros et al. |
| 6,039,761 A | 3/2000 | Li |
| 6,045,579 A | 4/2000 | Hochshuler |
| 6,049,026 A | 4/2000 | Muschler |
| 6,056,749 A | 5/2000 | Kuslich |
| 6,066,175 A | 5/2000 | Henderson et al. |
| 6,086,593 A | 7/2000 | Bonutti |
| 6,093,205 A | 7/2000 | McLeod |
| 6,099,531 A | 8/2000 | Bonutti |
| 6,102,950 A | 8/2000 | Vaccaro |
| 6,106,557 A | 8/2000 | Robioneck et al. |
| 6,117,174 A | 9/2000 | Nolan |
| 6,120,503 A | 9/2000 | Michelson |
| 6,126,689 A | 10/2000 | Brett |
| 6,127,597 A | 10/2000 | Beyar et al. |
| 6,129,763 A | 10/2000 | Chauvin et al. |
| 6,139,550 A | 10/2000 | Michelson |
| 6,146,387 A | 11/2000 | Trott et al. |
| 6,156,037 A | 12/2000 | LeHuec |
| 6,159,211 A | 12/2000 | Boriani |
| 6,159,244 A | 12/2000 | Suddaby |
| 6,174,311 B1 | 1/2001 | Branch et al. |
| 6,176,882 B1 | 1/2001 | Biedermann et al. |
| 6,179,794 B1 | 1/2001 | Burras |
| 6,179,873 B1 | 1/2001 | Zientek |
| 6,179,875 B1 | 1/2001 | Von Strempel |
| 6,183,517 B1 | 2/2001 | Suddaby |
| 6,190,414 B1 | 2/2001 | Young et al. |
| 6,193,757 B1 | 2/2001 | Foley et al. |
| 6,200,306 B1 | 3/2001 | Klostermeyer |
| 6,206,922 B1 | 3/2001 | Zdeblick |
| 6,224,602 B1 | 5/2001 | Hayes |
| 6,231,610 B1 | 5/2001 | Geisler |
| 6,235,059 B1 | 5/2001 | Benezech et al. |
| 6,296,647 B1 | 10/2001 | Robioneck et al. |
| 6,302,914 B1 | 10/2001 | Michelson |
| 6,306,170 B2 | 10/2001 | Ray |
| 6,330,845 B1 | 12/2001 | Meulink |
| 6,332,895 B1 | 12/2001 | Suddaby |
| 6,336,928 B1 | 1/2002 | Guerin |
| 6,342,055 B1 | 1/2002 | Eisermann |
| 6,342,074 B1 | 1/2002 | Simpson |
| 6,364,880 B1 | 4/2002 | Michelson |
| 6,368,351 B1 | 4/2002 | Glenn et al. |
| 6,375,462 B2 | 4/2002 | Glenn et al. |
| 6,375,682 B1 | 4/2002 | Fleischmann et al. |
| 6,387,130 B1 | 5/2002 | Stone |
| 6,395,031 B1 | 5/2002 | Foley et al. |
| 6,406,478 B1 | 6/2002 | Kuo |
| 6,409,766 B1 | 6/2002 | Brett |
| 6,413,278 B1 | 7/2002 | Marchosky |
| 6,419,705 B1 | 7/2002 | Erickson |
| 6,419,706 B1 | 7/2002 | Graf |
| 6,423,063 B1 | 7/2002 | Bonutti |
| 6,428,575 B2 | 8/2002 | Koo |

(56) References Cited

U.S. PATENT DOCUMENTS

| | | |
|---|---|---|
| 6,432,106 B1 | 8/2002 | Fraser |
| 6,436,140 B1 | 8/2002 | Liu et al. |
| 6,447,544 B1 | 9/2002 | Michelson |
| 6,447,546 B1 | 9/2002 | Bramlet |
| 6,454,769 B2 | 9/2002 | Wagner |
| 6,454,806 B1 | 9/2002 | Cohen et al. |
| 6,454,807 B1 | 9/2002 | Jackson |
| 6,461,359 B1 | 10/2002 | Tribus |
| 6,471,724 B2 | 10/2002 | Zdeblick |
| 6,488,710 B2 | 12/2002 | Besselink |
| 6,508,818 B2 | 1/2003 | Steiner et al. |
| 6,527,804 B1 | 3/2003 | Gauchet et al. |
| 6,558,387 B2 | 5/2003 | Errico |
| 6,558,423 B1 | 5/2003 | Michelson |
| 6,558,424 B2 | 5/2003 | Thalgott |
| 6,562,073 B2 | 5/2003 | Foley |
| 6,562,074 B2 | 5/2003 | Gerbec et al. |
| 6,565,570 B2 | 5/2003 | Sterett |
| 6,572,619 B2 | 6/2003 | Santilli |
| 6,579,290 B1 | 6/2003 | Hardcastle et al. |
| 6,582,468 B1 | 6/2003 | Gauchet |
| 6,602,257 B1 | 8/2003 | Thramann |
| 6,610,094 B2 | 8/2003 | Husson |
| 6,629,998 B1 | 10/2003 | Lin |
| 6,641,614 B1 | 11/2003 | Wagner et al. |
| 6,648,917 B2 | 11/2003 | Gerbec et al. |
| 6,676,665 B2 | 1/2004 | Foley et al. |
| 6,682,563 B2 | 1/2004 | Scharf |
| 6,695,846 B2 | 2/2004 | Richelsoph |
| 6,706,070 B1 | 3/2004 | Wagner et al. |
| 6,719,796 B2 | 4/2004 | Cohen et al. |
| 6,723,126 B1 | 4/2004 | Berry |
| 6,730,125 B1 | 5/2004 | Lin |
| 6,730,127 B2 | 5/2004 | Michelson |
| 6,733,531 B1 | 5/2004 | Trieu |
| 6,733,532 B1 | 5/2004 | Gauchet et al. |
| 6,736,850 B2 | 5/2004 | Davis |
| 6,743,255 B2 | 6/2004 | Ferree |
| 6,743,257 B2 | 6/2004 | Castro |
| 6,745,255 B2 | 6/2004 | Yen et al. |
| 6,761,738 B1 | 7/2004 | Boyd |
| 6,770,096 B2 | 8/2004 | Bolger |
| 6,773,437 B2 | 8/2004 | Ogilvie |
| 6,776,781 B1 | 8/2004 | Uwaydah |
| 6,805,714 B2 | 10/2004 | Sutcliffe |
| 6,808,537 B2 | 10/2004 | Michelson |
| 6,824,564 B2 | 11/2004 | Crozet |
| 6,824,565 B2 | 11/2004 | Muhanna et al. |
| 6,833,006 B2 | 12/2004 | Foley et al. |
| 6,835,208 B2 | 12/2004 | Marchosky |
| 6,837,905 B1 | 1/2005 | Lieberman |
| 6,849,093 B2 | 2/2005 | Michelson |
| 6,855,167 B2 | 2/2005 | Shimp |
| 6,863,673 B2 | 3/2005 | Gerbec et al. |
| 6,890,335 B2 | 5/2005 | Grabowski |
| 6,890,355 B2 | 5/2005 | Michelson |
| 6,893,464 B2 | 5/2005 | Kiester |
| 6,945,973 B2 | 9/2005 | Bray |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 6,972,019 B2 | 12/2005 | Michelson |
| 6,974,479 B2 | 12/2005 | Trieu |
| 6,974,480 B2 | 12/2005 | Messerli et al. |
| 6,984,234 B2 | 1/2006 | Bray |
| 7,001,385 B2 | 2/2006 | Bonutti |
| 7,018,412 B2 | 3/2006 | Ferreira et al. |
| 7,018,416 B2 | 3/2006 | Hanson et al. |
| 7,033,394 B2 | 4/2006 | Michelson |
| 7,037,339 B2 | 5/2006 | Houfburg et al. |
| 7,041,135 B2 | 5/2006 | Michelson |
| 7,044,971 B2 | 5/2006 | Suddaby |
| 7,056,341 B2 | 6/2006 | Crozet |
| 7,063,491 B2 | 6/2006 | French |
| 7,070,598 B2 | 7/2006 | Lim et al. |
| 7,077,864 B2 | 7/2006 | Byrd, III |
| 7,083,650 B2 | 8/2006 | Moskowitz et al. |
| 7,087,055 B2 | 8/2006 | Lim et al. |
| 7,094,257 B2 | 8/2006 | Mujwid et al. |
| 7,112,222 B2 | 9/2006 | Fraser |
| 7,112,223 B2 | 9/2006 | Davis |
| 7,135,024 B2 | 11/2006 | Cook |
| 7,135,043 B2 | 11/2006 | Nakahara |
| D536,096 S | 1/2007 | Hoogland |
| 7,163,561 B2 | 1/2007 | Michelson |
| 7,172,627 B2 | 2/2007 | Fiere et al. |
| 7,211,112 B2 | 5/2007 | Baynham et al. |
| 7,217,293 B2 | 5/2007 | Branch |
| 7,220,280 B2 | 5/2007 | Kast et al. |
| 7,223,292 B2 | 5/2007 | Messerli et al. |
| 7,226,482 B2 | 6/2007 | Messerli |
| 7,226,483 B2 | 6/2007 | Gerber et al. |
| 7,232,463 B2 | 6/2007 | Falahee |
| 7,232,464 B2 | 6/2007 | Mathieu |
| 7,235,101 B2 | 6/2007 | Berry et al. |
| 7,238,203 B2 | 7/2007 | Bagga |
| 7,238,206 B2 | 7/2007 | Lange |
| 7,255,698 B2 | 8/2007 | Michelson |
| 7,276,081 B1 | 10/2007 | Coates |
| 7,288,094 B2 | 10/2007 | Lindemann |
| 7,288,095 B2 | 10/2007 | Baynam et al. |
| 7,288,114 B2 | 10/2007 | Lange |
| 7,306,605 B2 | 12/2007 | Ross |
| 7,309,358 B2 | 12/2007 | Berry |
| 7,311,734 B2 | 12/2007 | Van Hoeck |
| 7,316,714 B2 | 1/2008 | Gordon |
| 7,318,839 B2 | 1/2008 | Malberg et al. |
| 7,323,011 B2 | 1/2008 | Shepard |
| 7,326,248 B2 | 2/2008 | Michelson |
| 7,332,209 B2 | 2/2008 | Yokouchi et al. |
| 7,338,525 B2 | 3/2008 | Ferree |
| 7,341,587 B2 | 3/2008 | Molz, IV |
| 7,341,590 B2 | 3/2008 | Ferree |
| 7,354,452 B2 | 4/2008 | Foley |
| 7,361,193 B2 | 4/2008 | Frey |
| 7,435,262 B2 | 10/2008 | Michelson |
| 7,438,715 B2 | 10/2008 | Doubler |
| 7,442,209 B2 | 10/2008 | Michelson |
| 7,452,370 B2 | 11/2008 | Anderson |
| D584,812 S | 1/2009 | Ries |
| 7,491,237 B2 | 2/2009 | Randall |
| 7,503,933 B2 | 3/2009 | Michelson |
| 7,507,241 B2 | 3/2009 | Levy et al. |
| 7,527,641 B2 | 5/2009 | Suh |
| 7,569,074 B2 | 8/2009 | Eiserman et al. |
| 7,594,931 B2 | 9/2009 | Louis |
| 7,594,932 B2 | 9/2009 | Aferzon et al. |
| 7,601,171 B2 | 10/2009 | Ainsworth et al. |
| 7,601,173 B2 | 10/2009 | Messerli |
| 7,608,062 B2 | 10/2009 | Sweeney |
| 7,618,456 B2 | 11/2009 | Mathieu |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,628,816 B2 | 12/2009 | Magerl et al. |
| 7,641,665 B2 | 1/2010 | Zubok |
| 7,655,042 B2 | 2/2010 | Foley et al. |
| 7,658,766 B2 | 2/2010 | Melkent |
| 7,662,182 B2 | 2/2010 | Zubok |
| 7,674,279 B2 | 3/2010 | Johnson |
| 7,691,147 B2 | 4/2010 | Gutlin et al. |
| 7,703,727 B2 | 4/2010 | Selness |
| 7,704,255 B2 | 4/2010 | Michelson |
| 7,722,612 B2 | 5/2010 | Sala et al. |
| 7,722,674 B1 | 5/2010 | Grotz |
| 7,726,002 B2 | 6/2010 | Shimp et al. |
| 7,749,270 B2 | 7/2010 | Peterman |
| 7,771,473 B2 | 8/2010 | Thramann |
| 7,785,368 B2 | 8/2010 | Schaller |
| 7,789,914 B2 | 9/2010 | Michelson |
| 7,794,502 B2 | 9/2010 | Michelson |
| 7,799,032 B2 | 9/2010 | Assell |
| 7,799,033 B2 | 9/2010 | Assell |

(56) References Cited

U.S. PATENT DOCUMENTS

| | | |
|---|---|---|
| 7,799,036 B2 | 9/2010 | Davison |
| D626,233 S | 10/2010 | Cipoletti |
| 7,814,429 B2 | 10/2010 | Buffet |
| 7,815,643 B2 | 10/2010 | Johnson et al. |
| 7,815,681 B2 | 10/2010 | Ferguson |
| 7,819,921 B2 | 10/2010 | Grotz |
| 7,824,410 B2 | 11/2010 | Simonson |
| 7,824,429 B2 | 11/2010 | Culbert |
| 7,824,445 B2 | 11/2010 | Biro et al. |
| 7,837,734 B2 | 11/2010 | Zucherman et al. |
| 7,846,183 B2 | 12/2010 | Blain |
| 7,846,206 B2 | 12/2010 | Oglaza et al. |
| 7,846,207 B2 | 12/2010 | Lechmann et al. |
| 7,846,210 B2 | 12/2010 | Perez-Cruet et al. |
| 7,850,695 B2 | 12/2010 | Pagliuca |
| 7,850,733 B2 | 12/2010 | Baynham et al. |
| 7,854,766 B2 | 12/2010 | Moskowitz et al. |
| 7,857,832 B2 | 12/2010 | Culbert |
| 7,862,590 B2 | 1/2011 | Lim |
| 7,862,595 B2 | 1/2011 | Foley |
| 7,862,616 B2 | 1/2011 | Lechmann et al. |
| 7,867,259 B2 | 1/2011 | Foley |
| 7,871,441 B2 | 1/2011 | Eckman |
| 7,874,980 B2 | 1/2011 | Sonnenschein et al. |
| 7,875,062 B2 | 1/2011 | Lindemann |
| 7,875,076 B2 | 1/2011 | Mathieu |
| 7,875,077 B2 | 1/2011 | Humphreys |
| 7,879,098 B1 | 2/2011 | Simmons |
| 7,883,531 B2 | 2/2011 | Coninck |
| 7,887,589 B2 | 2/2011 | Glenn et al. |
| 7,887,591 B2 | 2/2011 | Aebi et al. |
| 7,887,595 B1 | 2/2011 | Pimenta |
| 7,892,171 B2 | 2/2011 | Davison |
| 7,892,249 B2 | 2/2011 | Davison |
| 7,909,877 B2 | 2/2011 | Aebi et al. |
| 7,901,438 B2 | 3/2011 | Culbert |
| 7,901,459 B2 | 3/2011 | Hodges |
| 7,909,870 B2 | 3/2011 | Kraus |
| 7,922,729 B2 | 4/2011 | Michelson |
| 7,931,689 B2 | 4/2011 | Hochschuler |
| 7,938,832 B2 | 5/2011 | Culbert |
| 7,951,199 B2 | 5/2011 | Miller |
| 7,985,231 B2 | 7/2011 | Sankaran |
| 7,993,403 B2 | 8/2011 | Foley et al. |
| 7,998,176 B2 | 8/2011 | Culbert |
| 8,002,808 B2 | 8/2011 | Morrison et al. |
| 8,007,523 B2 | 8/2011 | Wagner |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,109,977 B2 | 2/2012 | Culbert |
| 8,114,088 B2 | 2/2012 | Miller |
| 8,118,871 B2 | 2/2012 | Gordon |
| 8,133,232 B2 | 3/2012 | Levy |
| 8,177,812 B2 | 5/2012 | Sankaran |
| 8,187,329 B2 | 5/2012 | Theofilos |
| 8,192,495 B2 | 6/2012 | Simpson et al. |
| 8,206,423 B2 | 6/2012 | Siegal |
| 8,216,312 B2 | 7/2012 | Gray |
| 8,221,501 B2 | 7/2012 | Eiserman et al. |
| 8,221,502 B2 | 7/2012 | Branch |
| 8,231,681 B2 | 7/2012 | Castleman et al. |
| 8,236,029 B2 | 8/2012 | Siegal |
| 8,236,058 B2 | 8/2012 | Fabian et al. |
| 8,241,328 B2 | 8/2012 | Siegal |
| 8,241,358 B2 | 8/2012 | Butler et al. |
| 8,246,622 B2 | 8/2012 | Siegal et al. |
| 8,257,440 B2 | 9/2012 | Gordon |
| 8,257,442 B2 | 9/2012 | Edie et al. |
| 8,262,736 B2 | 9/2012 | Michelson |
| 8,267,939 B2 | 9/2012 | Cipoletti et al. |
| 8,273,128 B2 | 9/2012 | Oh et al. |
| 8,273,129 B2 | 9/2012 | Baynham |
| 8,287,599 B2 | 10/2012 | McGuckin |
| 8,303,663 B2 | 11/2012 | Jimenez et al. |
| 8,317,866 B2 | 11/2012 | Palmatier |
| 8,323,342 B2 | 12/2012 | Schwab |
| 8,323,345 B2 | 12/2012 | Sledge |
| 8,328,812 B2 | 12/2012 | Siegal et al. |
| 8,328,852 B2 | 12/2012 | Zehavi et al. |
| 8,336,559 B2 | 12/2012 | Kallabat et al. |
| 8,337,559 B2 | 12/2012 | Hansell et al. |
| 8,343,219 B2 | 1/2013 | Allain |
| 8,349,015 B2 | 1/2013 | Allain |
| 8,353,961 B2 | 1/2013 | McClintock |
| 8,357,200 B2 | 1/2013 | Adi |
| 8,366,777 B2 | 2/2013 | Matthis |
| 8,382,842 B2 | 2/2013 | Greenhalgh et al. |
| 8,394,129 B2 | 3/2013 | Morgenstern Lopez |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,454,694 B2 | 6/2013 | Armstrong et al. |
| 8,460,385 B1 | 6/2013 | Wensel |
| 8,460,387 B2 | 6/2013 | Theofilos |
| 8,465,524 B2 | 6/2013 | Siegal |
| 8,470,044 B2 | 6/2013 | Bertholet et al. |
| 8,480,747 B2 | 7/2013 | Melkent et al. |
| 8,486,109 B2 | 7/2013 | Siegal |
| 8,486,148 B2 | 7/2013 | Butler et al. |
| 8,491,658 B1 | 7/2013 | Etminan |
| 8,491,659 B2 | 7/2013 | Weiman |
| 8,496,691 B2 | 7/2013 | Blain |
| 8,496,708 B2 | 7/2013 | Blain |
| 8,500,783 B2 | 8/2013 | Baynham |
| 8,506,635 B2 | 8/2013 | Palmatier et al. |
| 8,518,087 B2 | 8/2013 | Morgenstern et al. |
| 8,518,120 B2 | 8/2013 | Glerum et al. |
| 8,540,769 B2 | 9/2013 | O'Neil |
| 8,551,173 B2 | 10/2013 | Lechmann et al. |
| 8,551,175 B1 | 10/2013 | Wensel |
| 8,556,979 B2 | 10/2013 | Glerum et al. |
| 8,562,651 B2 | 10/2013 | Metcalf et al. |
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | Mclaughlin et al. |
| 8,597,330 B2 | 12/2013 | Siegal |
| 8,597,333 B2 | 12/2013 | Morgenstern Lopez |
| 8,603,170 B2 | 12/2013 | Cipoletti et al. |
| 8,613,772 B2 | 12/2013 | Bray et al. |
| 8,617,245 B2 | 12/2013 | Brett |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,765 B2 | 2/2014 | Muhanna |
| 8,663,329 B2 | 3/2014 | Ernst |
| 8,668,740 B2 | 3/2014 | Rhoda et al. |
| 8,672,977 B2 | 3/2014 | Siegal et al. |
| 8,679,183 B2 | 3/2014 | Glerum et al. |
| 8,685,098 B2 | 4/2014 | Glerum et al. |
| 8,690,928 B1 | 4/2014 | Walkenhorst et al. |
| 8,690,948 B2 | 4/2014 | Armstrong et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,747,443 B2 | 6/2014 | Aferzon |
| 8,753,398 B2 | 6/2014 | Gordon et al. |
| 8,758,439 B2 | 6/2014 | Linares |
| 8,764,831 B2 | 7/2014 | Lechmann |
| 8,771,360 B2 | 7/2014 | Jimenez et al. |
| 8,777,993 B2 | 7/2014 | Siegal et al. |
| 8,778,025 B2 | 7/2014 | Ragab et al. |
| 8,795,366 B2 | 8/2014 | Varela |
| 8,821,555 B2 | 9/2014 | Bae |
| 8,828,085 B1 | 9/2014 | Jensen |

(56) References Cited

U.S. PATENT DOCUMENTS

| | | |
|---|---|---|
| 8,845,638 B2 | 9/2014 | Siegal et al. |
| 8,845,731 B2 | 9/2014 | Weiman |
| 8,845,732 B2 | 9/2014 | Weiman |
| 8,845,734 B2 | 9/2014 | Weiman |
| 8,852,242 B2 | 10/2014 | Morgenstern Lopez |
| 8,852,243 B2 | 10/2014 | Morgenstern Lopez |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,235 B2 | 12/2014 | Siegal |
| 8,900,307 B2 | 12/2014 | Hawkins et al. |
| 8,906,098 B2 | 12/2014 | Siegal |
| 8,926,704 B2 | 1/2015 | Glerum |
| 8,932,358 B1 | 1/2015 | Nehls |
| 8,932,359 B2 | 1/2015 | Brett |
| 8,936,641 B2 | 1/2015 | Cain |
| 8,940,052 B2 | 1/2015 | Lechmann et al. |
| 8,956,416 B2 | 1/2015 | Brett |
| 9,005,293 B2 | 2/2015 | McCarthy |
| 8,986,387 B1 | 3/2015 | To et al. |
| 9,005,291 B2 | 4/2015 | Loebl et al. |
| 9,005,295 B2 | 4/2015 | Kueenzi et al. |
| 9,017,408 B2 | 4/2015 | Siegal |
| 9,017,413 B2 | 4/2015 | Siegal |
| 9,039,767 B2 | 5/2015 | Raymond et al. |
| 9,039,771 B2 | 5/2015 | Glerum et al. |
| 9,044,334 B2 | 6/2015 | Siegal |
| 9,060,876 B1 | 6/2015 | To et al. |
| 9,078,767 B1 | 7/2015 | Mclean |
| 9,091,488 B2 | 8/2015 | Malandain |
| 9,095,446 B2 | 8/2015 | Landry et al. |
| 9,095,447 B2 | 8/2015 | Barreiro et al. |
| 9,101,489 B2 | 8/2015 | Protopsaltis et al. |
| 9,107,766 B1 | 8/2015 | Mclean et al. |
| 9,138,330 B2 | 9/2015 | Hansell et al. |
| 9,192,419 B2 | 11/2015 | McDonough |
| 9,248,028 B2 | 2/2016 | Gamache |
| 9,254,138 B2 | 2/2016 | Siegal |
| 9,265,546 B2 | 2/2016 | Blain |
| 9,265,621 B2 | 2/2016 | Voellmicke |
| 9,271,836 B2 | 3/2016 | Pavento |
| 9,277,928 B2 | 3/2016 | Morgenstern Lopez |
| 9,278,009 B2 | 3/2016 | Bray et al. |
| 9,283,091 B2 | 3/2016 | Melkent |
| 9,283,092 B2 | 3/2016 | Siegal et al. |
| 9,289,311 B1 | 3/2016 | Whipple |
| 9,295,562 B2 | 3/2016 | Lechmann |
| 9,364,272 B2 | 6/2016 | Binder et al. |
| 9,402,735 B2 | 8/2016 | McDonough |
| 9,402,738 B2 | 8/2016 | Niemic |
| 9,408,712 B2 | 8/2016 | Siegal et al. |
| 9,414,934 B2 | 8/2016 | Cain |
| 9,433,510 B2 | 9/2016 | Lechmann |
| 9,492,286 B2 | 11/2016 | Biedermann et al. |
| 9,597,197 B2 | 3/2017 | Lechmann |
| 9,662,225 B2 | 5/2017 | Pavento |
| 9,668,877 B2 | 6/2017 | Pavento |
| 9,848,992 B2 | 12/2017 | McDonough |
| 9,867,718 B2 | 1/2018 | Schmura |
| 2001/0031968 A1 | 10/2001 | Dorchak et al. |
| 2001/0032020 A1 | 10/2001 | Besselink |
| 2002/0029044 A1 | 3/2002 | Monassevitch |
| 2002/0029082 A1 | 3/2002 | Muhanna |
| 2002/0068976 A1 | 6/2002 | Jackson |
| 2002/0068977 A1 | 6/2002 | Jackson |
| 2002/0095155 A1 | 7/2002 | Michelson |
| 2002/0099376 A1* | 7/2002 | Michelson ............ 606/61 |
| 2002/0128716 A1 | 9/2002 | Cohen et al. |
| 2002/0138146 A1 | 9/2002 | Jackson |
| 2002/0143328 A1 | 10/2002 | Shulzas |
| 2002/0151976 A1 | 10/2002 | Foley et al. |
| 2002/0156475 A1 | 10/2002 | Lerch et al. |
| 2002/0165612 A1 | 11/2002 | Gerber |
| 2003/0004575 A1 | 1/2003 | Erickson |
| 2003/0004576 A1 | 1/2003 | Thalgott |
| 2003/0023305 A1 | 1/2003 | McKay |
| 2003/0028197 A1 | 2/2003 | Hanson |
| 2003/0040799 A1 | 2/2003 | Boyd |
| 2003/0045940 A1 | 3/2003 | Eberlein |
| 2003/0050645 A1 | 3/2003 | Parker |
| 2003/0065396 A1 | 4/2003 | Michelson |
| 2003/0078667 A1 | 4/2003 | Manasas et al. |
| 2003/0083748 A1 | 5/2003 | Lee et al. |
| 2003/0100949 A1 | 5/2003 | Michelson |
| 2003/0125739 A1 | 7/2003 | Bagga |
| 2003/0130739 A1 | 7/2003 | Gerbec et al. |
| 2003/0135275 A1 | 7/2003 | Garcia |
| 2003/0139812 A1 | 7/2003 | Garcia |
| 2003/0139813 A1 | 7/2003 | Messerli et al. |
| 2003/0153975 A1 | 8/2003 | Byrd |
| 2003/0158555 A1 | 8/2003 | Sanders |
| 2003/0187440 A1 | 10/2003 | Richelsoph et al. |
| 2003/0187506 A1 | 10/2003 | Ross |
| 2003/0195632 A1 | 10/2003 | Foley |
| 2003/0208203 A1 | 11/2003 | Lim |
| 2003/0225409 A1 | 12/2003 | Freid |
| 2003/0233145 A1 | 12/2003 | Landry et al. |
| 2004/0006391 A1 | 1/2004 | Reiley |
| 2004/0024464 A1 | 2/2004 | Errico |
| 2004/0030387 A1 | 2/2004 | Landry et al. |
| 2004/0034430 A1 | 2/2004 | Falahee |
| 2004/0064144 A1 | 4/2004 | Johnson et al. |
| 2004/0073213 A1 | 4/2004 | Serhan |
| 2004/0087947 A1 | 5/2004 | Lim |
| 2004/0088055 A1 | 5/2004 | Hanson et al. |
| 2004/0092929 A1 | 5/2004 | Zindrick |
| 2004/0093083 A1 | 5/2004 | Branch |
| 2004/0106996 A1 | 6/2004 | Liu et al. |
| 2004/0111089 A1 | 6/2004 | Stevens et al. |
| 2004/0127902 A1 | 7/2004 | Suzuki |
| 2004/0127990 A1 | 7/2004 | Bartish |
| 2004/0127991 A1 | 7/2004 | Ferree |
| 2004/0138662 A1 | 7/2004 | Landry et al. |
| 2004/0153065 A1 | 8/2004 | Kim |
| 2004/0153072 A1 | 8/2004 | Bonutti |
| 2004/0153156 A1 | 8/2004 | Cohen et al. |
| 2004/0153160 A1 | 8/2004 | Carrasco |
| 2004/0162618 A1 | 8/2004 | Mujwid et al. |
| 2004/0167625 A1 | 8/2004 | Beyar et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0193269 A1 | 9/2004 | Fraser et al. |
| 2004/0199253 A1 | 10/2004 | Link |
| 2004/0199254 A1 | 10/2004 | Louis |
| 2004/0210219 A1 | 10/2004 | Bray |
| 2004/0230309 A1 | 11/2004 | DiMauro |
| 2004/0249377 A1 | 12/2004 | Kaes |
| 2004/0254644 A1 | 12/2004 | Taylor |
| 2004/0260286 A1 | 12/2004 | Ferree |
| 2005/0021144 A1 | 1/2005 | Malberg et al. |
| 2005/0033433 A1 | 2/2005 | Michelson |
| 2005/0038513 A1 | 2/2005 | Michelson |
| 2005/0038515 A1 | 2/2005 | Kunzler |
| 2005/0043800 A1 | 2/2005 | Paul et al. |
| 2005/0065608 A1 | 3/2005 | Michelson |
| 2005/0071006 A1 | 3/2005 | Kirschman |
| 2005/0071008 A1 | 3/2005 | Kirschman |
| 2005/0085913 A1 | 4/2005 | Fraser |
| 2005/0096657 A1 | 5/2005 | Autericque |
| 2005/0101960 A1 | 5/2005 | Fiere |
| 2005/0113916 A1 | 5/2005 | Branch |
| 2005/0113917 A1 | 5/2005 | Chae et al. |
| 2005/0113920 A1 | 5/2005 | Foley et al. |
| 2005/0125062 A1 | 6/2005 | Biedermann et al. |
| 2005/0143749 A1 | 6/2005 | Zalenski |
| 2005/0143827 A1 | 6/2005 | Globerman et al. |
| 2005/0149192 A1 | 7/2005 | Zucherman |
| 2005/0149193 A1 | 7/2005 | Zucherman |
| 2005/0154391 A1 | 7/2005 | Doherty et al. |
| 2005/0159813 A1 | 7/2005 | Molz |
| 2005/0177236 A1 | 8/2005 | Mathieu et al. |
| 2005/0177240 A1 | 8/2005 | Blain |

(56) References Cited

U.S. PATENT DOCUMENTS

| | | |
|---|---|---|
| 2005/0177245 A1 | 8/2005 | Leatherbury |
| 2005/0182416 A1 | 8/2005 | Lim et al. |
| 2005/0203515 A1 | 9/2005 | Doherty |
| 2005/0209696 A1 | 9/2005 | Lin et al. |
| 2005/0222681 A1 | 10/2005 | Richley et al. |
| 2005/0251260 A1 | 11/2005 | Gerber |
| 2005/0256576 A1 | 11/2005 | Moskowitz et al. |
| 2005/0261768 A1 | 11/2005 | Trieu |
| 2005/0261769 A1 | 11/2005 | Moskowitz et al. |
| 2005/0277938 A1 | 12/2005 | Parsons |
| 2005/0278026 A1 | 12/2005 | Gordon et al. |
| 2005/0278036 A1 | 12/2005 | Leonard |
| 2006/0025860 A1 | 2/2006 | Li |
| 2006/0030851 A1 | 2/2006 | Bray |
| 2006/0058801 A1 | 3/2006 | Schlienger et al. |
| 2006/0058876 A1 | 3/2006 | McKinley |
| 2006/0079961 A1 | 4/2006 | Michelson |
| 2006/0085071 A1 | 4/2006 | Lechmann et al. |
| 2006/0100706 A1 | 5/2006 | Shadduck et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0129424 A1 | 6/2006 | Chan |
| 2006/0136062 A1 | 6/2006 | DiNello et al. |
| 2006/0142759 A1 | 6/2006 | Amin |
| 2006/0142765 A9 | 6/2006 | Dixon |
| 2006/0142858 A1 | 6/2006 | Colleran et al. |
| 2006/0142863 A1 | 6/2006 | Fraser |
| 2006/0152863 A1 | 6/2006 | Fraser |
| 2006/0178745 A1 | 8/2006 | Bartish |
| 2006/0190083 A1 | 8/2006 | Arnin |
| 2006/0206207 A1 | 9/2006 | Dryer et al. |
| 2006/0211952 A1 | 9/2006 | Kennedy |
| 2006/0229609 A1 | 10/2006 | Wang |
| 2006/0229725 A1 | 10/2006 | Lechmann et al. |
| 2006/0229729 A1 | 10/2006 | Gordon et al. |
| 2006/0235403 A1 | 10/2006 | Blain |
| 2006/0235409 A1 | 10/2006 | Blain |
| 2006/0235411 A1 | 10/2006 | Blain et al. |
| 2006/0235518 A1 | 10/2006 | Blain |
| 2006/0235531 A1 | 10/2006 | Buettner |
| 2006/0235535 A1 | 10/2006 | Ferree |
| 2006/0241597 A1 | 10/2006 | Mitchell et al. |
| 2006/0241761 A1 | 10/2006 | Gately |
| 2006/0247650 A1 | 11/2006 | Yerby et al. |
| 2006/0253201 A1 | 11/2006 | Mcluen |
| 2006/0259147 A1 | 11/2006 | Krishna |
| 2006/0265068 A1 | 11/2006 | Schwab |
| 2006/0265075 A1 | 11/2006 | Baumgartner et al. |
| 2006/0265077 A1 | 11/2006 | Zwirkoski |
| 2006/0293753 A1 | 12/2006 | Thramann |
| 2007/0010886 A1 | 1/2007 | Banick et al. |
| 2007/0049941 A1 | 3/2007 | Thramann |
| 2007/0055252 A1 | 3/2007 | Blain et al. |
| 2007/0055377 A1 | 3/2007 | Hanson et al. |
| 2007/0067035 A1 | 3/2007 | Falahee |
| 2007/0073398 A1 | 3/2007 | Fabian et al. |
| 2007/0106384 A1 | 5/2007 | Bray |
| 2007/0106388 A1 | 5/2007 | Michelson |
| 2007/0118222 A1 | 5/2007 | Lang |
| 2007/0129804 A1 | 6/2007 | Bentley |
| 2007/0149978 A1 | 6/2007 | Shezifi et al. |
| 2007/0162138 A1 | 7/2007 | Heinz |
| 2007/0173939 A1 | 7/2007 | Kim et al. |
| 2007/0191959 A1 | 8/2007 | Hartmann et al. |
| 2007/0198016 A1 | 8/2007 | Zang et al. |
| 2007/0198089 A1 | 8/2007 | Moskowitz et al. |
| 2007/0208423 A1 | 9/2007 | Messerli et al. |
| 2007/0213737 A1 | 9/2007 | Schemmerhom et al. |
| 2007/0213820 A1 | 9/2007 | Magerl |
| 2007/0219634 A1 | 9/2007 | Greenhalgh et al. |
| 2007/0219635 A1 | 9/2007 | Mathieu et al. |
| 2007/0233118 A1 | 10/2007 | Mclain |
| 2007/0233244 A1 | 10/2007 | Lopez et al. |
| 2007/0233253 A1 | 10/2007 | Bray |
| 2007/0233254 A1 | 10/2007 | Grotz |
| 2007/0233261 A1 | 10/2007 | Lopez et al. |
| 2007/0233263 A1 | 10/2007 | Melkent |
| 2007/0250167 A1 | 10/2007 | Bray |
| 2007/0255416 A1 | 11/2007 | Melkent |
| 2007/0265631 A1 | 11/2007 | Fox |
| 2007/0270957 A1 | 11/2007 | Heinz |
| 2007/0270965 A1 | 11/2007 | Ferguson |
| 2007/0270968 A1 | 11/2007 | Baynham et al. |
| 2007/0276375 A1 | 11/2007 | Rapp |
| 2007/0276490 A1 | 11/2007 | Mateyka |
| 2007/0282443 A1 | 12/2007 | Globerman et al. |
| 2007/0282449 A1 | 12/2007 | De Villiers et al. |
| 2007/0293948 A1 | 12/2007 | Bagga |
| 2007/0299521 A1 | 12/2007 | Glenn |
| 2008/0009877 A1 | 1/2008 | Sankaran et al. |
| 2008/0015694 A1 | 1/2008 | Tribus |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link |
| 2008/0033440 A1 | 2/2008 | Moskowitz |
| 2008/0033480 A1 | 2/2008 | Hardert |
| 2008/0051890 A1 | 2/2008 | Waugh |
| 2008/0051897 A1 | 2/2008 | Lopez et al. |
| 2008/0058944 A1 | 3/2008 | Duplessis et al. |
| 2008/0065219 A1 | 3/2008 | Dye |
| 2008/0077247 A1 | 3/2008 | Murillo |
| 2008/0082173 A1 | 4/2008 | Delurio |
| 2008/0097436 A1 | 4/2008 | Culbert |
| 2008/0103597 A1 | 5/2008 | Lechman et al. |
| 2008/0103598 A1 | 5/2008 | Trudeau et al. |
| 2008/0109005 A1 | 5/2008 | Trudeau et al. |
| 2008/0125865 A1 | 5/2008 | Abdelgany |
| 2008/0132949 A1 | 6/2008 | Aferzon |
| 2008/0132958 A1 | 6/2008 | Pech |
| 2008/0133012 A1 | 6/2008 | McGuckin |
| 2008/0133014 A1 | 6/2008 | Gately et al. |
| 2008/0140207 A1 | 6/2008 | Olmos |
| 2008/0147193 A1 | 6/2008 | Matthis et al. |
| 2008/0161925 A1 | 7/2008 | Brittan |
| 2008/0167657 A1 | 7/2008 | Greenhalgh |
| 2008/0167666 A1 | 7/2008 | Fiere |
| 2008/0177307 A1 | 7/2008 | Moskowitz |
| 2008/0177388 A1 | 7/2008 | Patterson et al. |
| 2008/0183204 A1 | 7/2008 | Greenhalgh et al. |
| 2008/0183294 A1 | 7/2008 | Adl |
| 2008/0195209 A1 | 8/2008 | Garcia et al. |
| 2008/0221690 A1 | 9/2008 | Chaput |
| 2008/0221694 A1 | 9/2008 | Warnick et al. |
| 2008/0234822 A1 | 9/2008 | Govil |
| 2008/0243136 A1 | 10/2008 | Prager |
| 2008/0243251 A1 | 10/2008 | Stad et al. |
| 2008/0243254 A1 | 10/2008 | Butler |
| 2008/0249575 A1 | 10/2008 | Waugh |
| 2008/0249622 A1 | 10/2008 | Gray |
| 2008/0249625 A1 | 10/2008 | Waugh |
| 2008/0255620 A1 | 10/2008 | Strauss |
| 2008/0269806 A1 | 10/2008 | Zhang |
| 2008/0269904 A1 | 10/2008 | Voorhies |
| 2008/0281425 A1 | 11/2008 | Thalgott |
| 2008/0294262 A1 | 11/2008 | Levieux |
| 2008/0300601 A1 | 12/2008 | Fabian et al. |
| 2008/0300634 A1 | 12/2008 | Gray |
| 2008/0306596 A1 | 12/2008 | Jones |
| 2008/0306598 A1 | 12/2008 | Hansen |
| 2008/0312698 A1 | 12/2008 | Bergeron |
| 2008/0312742 A1 | 12/2008 | Abernathie |
| 2008/0312743 A1 | 12/2008 | Vila et al. |
| 2009/0005873 A1 | 1/2009 | Slivka et al. |
| 2009/0012529 A1 | 1/2009 | Blain |
| 2009/0030421 A1 | 1/2009 | Hawkins |
| 2009/0030423 A1 | 1/2009 | Puno |
| 2009/0030519 A1 | 1/2009 | Falahee |
| 2009/0030520 A1 | 1/2009 | Biedermann |
| 2009/0048631 A1 | 2/2009 | Bhatnagar |
| 2009/0054991 A1 | 2/2009 | Biyani |
| 2009/0062921 A1 | 3/2009 | Michelson |
| 2009/0076610 A1 | 3/2009 | Afzal |

(56) References Cited

U.S. PATENT DOCUMENTS

| | | |
|---|---|---|
| 2009/0088849 A1 | 4/2009 | Armstrong |
| 2009/0099554 A1 | 4/2009 | Forster |
| 2009/0099568 A1 | 4/2009 | Lowry et al. |
| 2009/0099610 A1 | 4/2009 | Johnson et al. |
| 2009/0099661 A1 | 4/2009 | Bhattacharya |
| 2009/0105771 A1 | 4/2009 | Lei |
| 2009/0105774 A1 | 4/2009 | Jones |
| 2009/0105830 A1 | 4/2009 | Jones |
| 2009/0105831 A1 | 4/2009 | Jones |
| 2009/0112320 A1 | 4/2009 | Kraus |
| 2009/0112324 A1 | 4/2009 | Refai et al. |
| 2009/0125028 A1 | 5/2009 | Teisen et al. |
| 2009/0131988 A1 | 5/2009 | Bush, Jr. |
| 2009/0132054 A1 | 5/2009 | Zeegers |
| 2009/0143859 A1 | 6/2009 | McClellan, III |
| 2009/0164020 A1 | 6/2009 | Janowski |
| 2009/0182428 A1 | 7/2009 | McClellan, III et al. |
| 2009/0182430 A1 | 7/2009 | Tyber |
| 2009/0192549 A1 | 7/2009 | Sanders |
| 2009/0192613 A1 | 7/2009 | Wing |
| 2009/0192614 A1 | 7/2009 | Beger |
| 2009/0192615 A1 | 7/2009 | Tyber |
| 2009/0192616 A1 | 7/2009 | Zielinski |
| 2009/0198245 A1* | 8/2009 | Phan .............................. 606/99 |
| 2009/0198287 A1 | 8/2009 | Chiu |
| 2009/0198339 A1 | 8/2009 | Kleiner et al. |
| 2009/0210062 A1 | 8/2009 | Thalgott |
| 2009/0210064 A1 | 8/2009 | Lechmann et al. |
| 2009/0222096 A1 | 9/2009 | Trieu |
| 2009/0222099 A1 | 9/2009 | Liu et al. |
| 2009/0224023 A1 | 9/2009 | Moskowitz |
| 2009/0234364 A1 | 9/2009 | Crook |
| 2009/0234398 A1 | 9/2009 | Chirico et al. |
| 2009/0240335 A1 | 9/2009 | Arcenio et al. |
| 2009/0248092 A1 | 10/2009 | Bellas |
| 2009/0248159 A1 | 10/2009 | Aflatoon |
| 2009/0259316 A1 | 10/2009 | Ginn |
| 2009/0265007 A1 | 10/2009 | Colleran |
| 2009/0270873 A1 | 10/2009 | Fabian |
| 2009/0287251 A1 | 11/2009 | Bae |
| 2009/0292361 A1 | 11/2009 | Lopez et al. |
| 2009/0306779 A1 | 12/2009 | Ahn |
| 2009/0326543 A1 | 12/2009 | Fabian |
| 2009/0326580 A1 | 12/2009 | Anderson |
| 2009/0326589 A1 | 12/2009 | Lemoine |
| 2010/0004747 A1 | 1/2010 | Lin |
| 2010/0016901 A1 | 1/2010 | Robinson |
| 2010/0016905 A1 | 1/2010 | Greenhalgh et al. |
| 2010/0016973 A1 | 1/2010 | De Villiers et al. |
| 2010/0023128 A1 | 1/2010 | Malberg |
| 2010/0024779 A1 | 2/2010 | Makita |
| 2010/0030334 A1 | 2/2010 | Molz, IV |
| 2010/0036496 A1 | 2/2010 | Yu |
| 2010/0042159 A1 | 2/2010 | Butler |
| 2010/0057206 A1 | 3/2010 | Duffield |
| 2010/0069969 A1 | 3/2010 | Ampuero |
| 2010/0070037 A1 | 3/2010 | Parry et al. |
| 2010/0087925 A1 | 4/2010 | Kostuik |
| 2010/0094424 A1 | 4/2010 | Woodburn |
| 2010/0106249 A1 | 4/2010 | Tyber |
| 2010/0125334 A1 | 5/2010 | Krueger |
| 2010/0137987 A1 | 6/2010 | Diao |
| 2010/0145457 A1 | 6/2010 | Felt |
| 2010/0145459 A1 | 6/2010 | McDonough |
| 2010/0145460 A1 | 6/2010 | McDonough |
| 2010/0179594 A1 | 7/2010 | Theofilos et al. |
| 2010/0179656 A1 | 7/2010 | Theofilos |
| 2010/0185287 A1 | 7/2010 | Allard et al. |
| 2010/0185289 A1 | 7/2010 | Kirwan |
| 2010/0204739 A1 | 8/2010 | Bae et al. |
| 2010/0204795 A1 | 8/2010 | Bae et al. |
| 2010/0217325 A1 | 8/2010 | Hochschuler et al. |
| 2010/0217393 A1 | 8/2010 | Theofilos |
| 2010/0234956 A1 | 8/2010 | Theofilos |
| 2010/0249935 A1 | 9/2010 | Slivka |
| 2010/0249937 A1 | 9/2010 | Slivka |
| 2010/0262240 A1 | 10/2010 | Chavatte et al. |
| 2010/0286777 A1 | 11/2010 | Errico |
| 2010/0286781 A1 | 11/2010 | Bullard |
| 2010/0286783 A1 | 11/2010 | Lechmann |
| 2010/0292696 A1 | 11/2010 | Chantelot |
| 2010/0292737 A1 | 11/2010 | Suh |
| 2010/0305704 A1 | 12/2010 | Messerli |
| 2010/0312345 A1 | 12/2010 | Duffield |
| 2010/0312346 A1 | 12/2010 | Kueenzi |
| 2010/0324607 A1 | 12/2010 | Duffield |
| 2011/0004308 A1 | 1/2011 | Marino et al. |
| 2011/0004310 A1 | 1/2011 | Michelson |
| 2011/0009908 A1 | 1/2011 | Ferguson |
| 2011/0009966 A1 | 1/2011 | Michelson |
| 2011/0015675 A1 | 1/2011 | Michelson |
| 2011/0015745 A1 | 1/2011 | Bucci |
| 2011/0015747 A1 | 1/2011 | McManus et al. |
| 2011/0029082 A1 | 2/2011 | Hall |
| 2011/0035011 A1 | 2/2011 | Cain |
| 2011/0082550 A1 | 4/2011 | Yeh |
| 2011/0082555 A1 | 4/2011 | Martz |
| 2011/0093074 A1 | 4/2011 | Martz |
| 2011/0098747 A1 | 4/2011 | Donner |
| 2011/0106159 A1 | 4/2011 | Donner et al. |
| 2011/0118843 A1 | 5/2011 | Mathieu et al. |
| 2011/0130835 A1 | 6/2011 | Ashley et al. |
| 2011/0130838 A1 | 6/2011 | Morgenstern et al. |
| 2011/0144692 A1 | 6/2011 | Saladin |
| 2011/0144703 A1 | 6/2011 | Krause |
| 2011/0144753 A1 | 6/2011 | Krause et al. |
| 2011/0166656 A1 | 7/2011 | Thalgott et al. |
| 2011/0172716 A1 | 7/2011 | Glerum |
| 2011/0184415 A1 | 7/2011 | Anderson |
| 2011/0185292 A1 | 7/2011 | Chawla |
| 2011/0190892 A1 | 8/2011 | Kirschman |
| 2011/0202136 A1 | 8/2011 | Brittan |
| 2011/0208311 A1 | 8/2011 | Janowski |
| 2011/0213421 A1 | 8/2011 | Janowski |
| 2011/0230971 A1 | 9/2011 | Donner |
| 2011/0251689 A1 | 9/2011 | Donner et al. |
| 2011/0270261 A1 | 11/2011 | Mast et al. |
| 2011/0282453 A1 | 11/2011 | Greenhalgh et al. |
| 2011/0295371 A1 | 12/2011 | Moskowitz |
| 2011/0301711 A1 | 12/2011 | Palmatier et al. |
| 2011/0301712 A1 | 12/2011 | Palmatier et al. |
| 2011/0319896 A1* | 12/2011 | Papenfuss et al. ............. 606/79 |
| 2011/0319898 A1* | 12/2011 | O'Neil ............... A61B 17/1671 606/84 |
| 2011/0319943 A1 | 12/2011 | Curran |
| 2011/0319998 A1 | 12/2011 | O'Neil |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0041559 A1 | 2/2012 | Melkent |
| 2012/0071977 A1 | 3/2012 | Oglaza et al. |
| 2012/0071980 A1 | 3/2012 | Purcell et al. |
| 2012/0078371 A1 | 3/2012 | Gamache |
| 2012/0078372 A1 | 3/2012 | Gamache |
| 2012/0078373 A1 | 3/2012 | Gamache |
| 2012/0083889 A1 | 3/2012 | Gamache |
| 2012/0101581 A1 | 4/2012 | Mathieu et al. |
| 2012/0109309 A1 | 5/2012 | Mathieu et al. |
| 2012/0109310 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0143336 A1 | 6/2012 | Aflatoon et al. |
| 2012/0150301 A1 | 6/2012 | Gamache |
| 2012/0150303 A1 | 6/2012 | Linares |
| 2012/0158143 A1 | 6/2012 | Shapiro |
| 2012/0185049 A1 | 6/2012 | Shapiro |
| 2012/0191190 A1 | 7/2012 | Trieu |
| 2012/0197401 A1 | 8/2012 | Duncan |
| 2012/0197403 A1 | 8/2012 | Duncan |
| 2012/0197405 A1 | 8/2012 | Cuevas et al. |
| 2012/0203230 A1* | 8/2012 | Adams ........................... 606/80 |

(56) References Cited

U.S. PATENT DOCUMENTS

| | | |
|---|---|---|
| 2012/0209331 A1 | 8/2012 | Michelson |
| 2012/0226319 A1 | 9/2012 | Armstrong |
| 2012/0226357 A1 | 9/2012 | Varela |
| 2012/0290097 A1 | 10/2012 | Bae |
| 2012/0310350 A1 | 12/2012 | Farris et al. |
| 2012/0310352 A1 | 12/2012 | DiMauro et al. |
| 2013/0030536 A1 | 1/2013 | Rhoda et al. |
| 2013/0041471 A1 | 2/2013 | Siegal |
| 2013/0060337 A1 | 3/2013 | Petersheim |
| 2013/0073044 A1 | 3/2013 | Gamache |
| 2013/0079883 A1 | 3/2013 | Butler |
| 2013/0085574 A1 | 3/2013 | Gamache |
| 2013/0085572 A1 | 4/2013 | Glerum et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0166027 A1 | 6/2013 | Bellas |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | Mcluen et al. |
| 2013/0211525 A1 | 8/2013 | Mcluen et al. |
| 2013/0211526 A1 | 8/2013 | Alheidt et al. |
| 2013/0238095 A1 | 9/2013 | Pavento et al. |
| 2013/0268080 A1 | 10/2013 | Melkent et al. |
| 2013/0325071 A1 | 10/2013 | Melkent |
| 2013/0310939 A1 | 11/2013 | Fabian |
| 2013/0345813 A1 | 12/2013 | Niemiec |
| 2014/0039623 A1 | 12/2013 | Frank |
| 2014/0025169 A1 | 1/2014 | Lechmann |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Lopez |
| 2014/0107786 A1 | 4/2014 | Geisler et al. |
| 2014/0114415 A1 | 4/2014 | Geisler |
| 2014/0114423 A1 | 4/2014 | Suedkamp et al. |
| 2014/0128977 A1 | 5/2014 | Glerum et al. |
| 2014/0135930 A1 | 5/2014 | Georges |
| 2014/0135934 A1 | 5/2014 | Georges |
| 2014/0142705 A1 | 5/2014 | Duffield |
| 2014/0142706 A1 | 5/2014 | Hansell et al. |
| 2014/0156009 A1 | 6/2014 | Armstrong |
| 2014/0163683 A1 | 6/2014 | Seifert et al. |
| 2014/0172103 A1 | 6/2014 | O'Neil |
| 2014/0172106 A1 | 6/2014 | To et al. |
| 2014/0180421 A1 | 6/2014 | Glerum et al. |
| 2014/0228959 A1 | 8/2014 | Niemiec et al. |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0277474 A1 | 9/2014 | Robinson et al. |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0012097 A1 | 1/2015 | Ibarra et al. |
| 2015/0045894 A1 | 2/2015 | Hawkins et al. |
| 2015/0094812 A1 | 4/2015 | Marden et al. |
| 2015/0094813 A1 | 4/2015 | Lechmann et al. |
| 2015/0112438 A1 | 4/2015 | Mclean |
| 2015/0182347 A1 | 7/2015 | Robinson |
| 2015/0250606 A1 | 9/2015 | Mclean |
| 2015/0257892 A1 | 9/2015 | Lechmann et al. |
| 2015/0297356 A1 | 10/2015 | Gamache |
| 2015/0313721 A1 | 11/2015 | Gamache |
| 2015/0374511 A1 | 12/2015 | Pavento |
| 2016/0128846 A1 | 2/2016 | Bellas et al. |
| 2016/0213487 A1 | 7/2016 | Wilson |
| 2016/0317317 A1 | 7/2016 | Wilson et al. |
| 2016/0324660 A1 | 11/2016 | Pavento |
| 2016/0324662 A1 | 11/2016 | McDonough et al. |
| 2017/0290674 A1 | 10/2017 | Olmos |
| 2017/0304068 A1 | 10/2017 | Bellas |
| 2017/0312090 A1 | 11/2017 | Sharabani |

FOREIGN PATENT DOCUMENTS

| | | |
|---|---|---|
| CN | 101909548 | 12/2010 |
| CN | 101951847 | 1/2011 |
| CN | 102164552 | 8/2011 |
| CN | 101087566 | 12/2017 |
| DE | 19710392 | 7/1999 |
| EP | 1609444 | 12/2005 |
| EP | 1683490 | 7/2008 |
| EP | 1506753 B1 | 9/2009 |
| EP | 2156812 | 2/2010 |
| EP | 1774926 | 6/2010 |
| EP | 1847240 | 11/2011 |
| GB | 2220729 | 1/1990 |
| GB | 2457673 | 8/2009 |
| JP | 2005524472 | 8/2005 |
| JP | 2008514362 | 5/2008 |
| WO | WO 1998/004217 | 2/1998 |
| WO | WO 1998004217 | 2/1998 |
| WO | WO 1999/052473 | 10/1999 |
| WO | WO 1999052473 | 10/1999 |
| WO | WO 1999/038463 | 11/1999 |
| WO | WO 1999038463 | 11/1999 |
| WO | WO 2001/008864 | 2/2001 |
| WO | WO 2001008864 | 2/2001 |
| WO | WO 2002/013732 | 5/2002 |
| WO | WO 2002013732 | 5/2002 |
| WO | WO 2003/003951 | 1/2003 |
| WO | WO 2003/005938 | 1/2003 |
| WO | WO 2003/005939 | 5/2003 |
| WO | WO 2003005939 | 5/2003 |
| WO | WO 2003/090650 | 11/2003 |
| WO | WO 2003090650 | 11/2003 |
| WO | WO 2004/069106 | 8/2004 |
| WO | WO 2004069106 | 8/2004 |
| WO | WO 2003/070128 | 10/2004 |
| WO | WO 2003070128 | 10/2004 |
| WO | WO 2005/020861 | 3/2005 |
| WO | WO 2005020861 | 3/2005 |
| WO | WO 2006/084057 | 8/2006 |
| WO | WO 2006084057 | 8/2006 |
| WO | WO 2007/003785 | 1/2007 |
| WO | WO 2007003785 | 1/2007 |
| WO | WO 2007/118856 | 10/2007 |
| WO | WO 2007118856 | 10/2007 |
| WO | WO 2007/098288 | 3/2008 |
| WO | WO 2007098288 | 3/2008 |
| WO | WO 2009/025841 | 2/2009 |
| WO | WO 2008/149223 | 4/2009 |
| WO | WO 2008149223 | 4/2009 |
| WO | WO 2009/064644 | 5/2009 |
| WO | WO 2009064644 | 5/2009 |
| WO | WO 2009/091775 | 9/2009 |
| WO | WO 2009091775 | 9/2009 |
| WO | WO 2009/136009 | 11/2009 |
| WO | WO 2010/028045 | 3/2010 |
| WO | WO 2010/033786 | 3/2010 |
| WO | WO 2010028045 | 3/2010 |
| WO | WO 2010054181 | 5/2010 |
| WO | WO 2010054208 | 5/2010 |
| WO | WO 2010/092893 | 8/2010 |
| WO | WO 2010092893 | 8/2010 |
| WO | WO 2010/121028 | 10/2010 |
| WO | WO 2010121028 | 12/2010 |
| WO | WO 2010/099239 | 1/2011 |
| WO | WO 2011/008864 | 1/2011 |
| WO | WO 2010099239 | 1/2011 |
| WO | WO 2011/080535 | 7/2011 |

(56) References Cited

FOREIGN PATENT DOCUMENTS

| | | |
|---|---|---|
| WO | WO 2011080535 | 7/2011 |
| WO | WO 2012/056119 | 5/2012 |
| WO | WO 2013/018062 | 2/2013 |
| WO | WO 2013018062 | 2/2013 |
| WO | WO 2013/096192 | 6/2013 |
| WO | WO 2013/191979 | 12/2013 |

OTHER PUBLICATIONS

Allcock, "Polyphosphazenes", The Encyclopedia of Polymer Science, vol. 13, pp. 31-41, Wiley Intersciences, John Wiley & Sons, (1988).

Cohn and Younes, "Biodegradable PEO/PLA Block Copolymers", Journal of Biomaterials Research, 1988, vol. 22, pp. 993-1009.

Cohn, "Polymer Preprints", ACS Division of Polymer Chemistry, vol. 30(1), 1989, p. 498, (e.g. PEO/PLA).

Heller, "Poly(Ortho Esters)", Handbook of Biodegradable Polymers, edited by Domb, et al, Hardwood Academic Press, pp. 99-118, 1997.

Kemnitzer and Kohn, "Degradable Polymers Derived From the Amino Acid L-Tyrosine", The Handbook of Biodegradable Polymers, edited by Domb, et. al., Hardwood Academic Press, 1997, pp. 251-272.

Vandorpe, "Biodegradable Polyphosphazenes for Biomeidcal Applications", The Handbook of Biodegradable Polymers, edited by Domb, et al, Hardwood Academic Press, 1997, pp. 161-182.

Allcock in the Encyclopedia of Polymer Science, vol. 13, pp. 31-41, Wiley Intersciences, John Wiley & Sons, 1988.

Cain, "New Stand-Alone Anterior Lumbar Interbody Fusion Device: Bioemechanical Comparison with Established Fixation Techniques", Spine, vol. 30, No. 23, pp. 2631-2636, 2005, Lippincott Williams & Wilkins Inc.

Gercek, "Subsidence of Stand-Alone Cervical Cages in Anterior Interbody Fusion: Warning", Eur Spine J., vol. 12, pp. 513-516, 2003, Springer-Verlag.

Heller in Handbook of Biodegradable Polymers, edited by Domb, et al, Hardwood Academic Press, pp. 99-118 (1997).

Humphries, "Anterior Fusion of the Lumbar Spine Using an Internal Fixative Device", Surgical Forum, vol. IX, pp. 770-773, American College of Surgeons, 1959, Chicago Illinois.

Cohn, Journal of Biomaterials Research, vol. 22, pp. 993-1009, 1988.

Kandziora, "Biomechanical Comparison of Cervical Spine Interbody Fusion Cages", Spine, vol. 26, No. 17, pp. 1850-1857, 2001, Lippincott Williams & Wilkins, Inc.

Kemnitzer and Kohn, in the Handbook of Biodegradable Polymers, edited by Domb, et. al., Hardwood Academic Press, pp. 251-272 (1997).

Oxland, "A Comparative Biomechanical Investigation of Anterior Lumbar Interbody Cages: Central and Bilateral Approaches", The Journal of Bone and Joint Surgery, pp. 383-393, vol. 82A, No. 3, Mar. 2000.

Pavlov, "Good Outcome and Restoration of Lordosis After Anterior Lumbar Interbody Fusion With Additional Posterior Fixation", Spine, vol. 29, No. 17, pp. 1893-1900, 2004, Lippincott Williams & Wilkins.

Pederson, "Thermal Assembly of a Biomimetic Mineral/Collagen Composite", Biomaterials, 2003, vol. 2, pp. 4881-4890, Elsevier.

Cohn, Polymer Preprints (ACS Division of Polymer Chemistry), vol. 30(1), p. 498, 1989.

Samandouras, "A New Anterior Cervical Instrumentation System Combining an Intradiscal Cage With an Integrated Plate", Spine, vol. 26, No. 10, pp. 1188-1192, 2001, Lippincott Williams and Watkins, Inc.

Vandorpe, et al in the Handbook of Biodegradable Polymers. edited by Domb, et al, Hardwood Academic Press, pp. 161-182 (1997).

Schmiedberg, Isoloation and characterization of metallic wear debris from a dynamic intervertebral disc prosthesis, J. Biomed. Mater. Res., vol. 28 Issue 11, 1277-1288, Nov. 1994.

\* cited by examiner

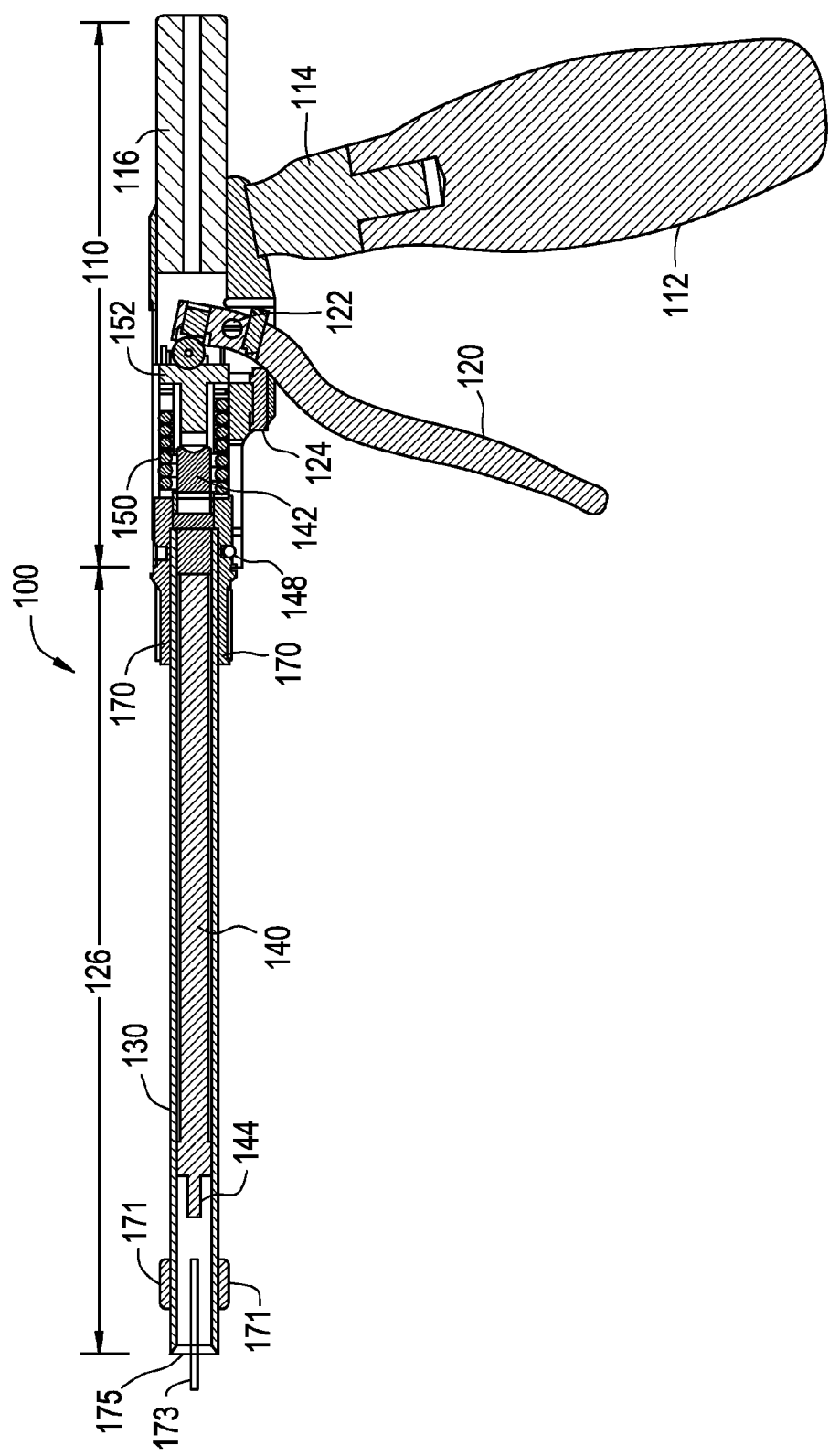

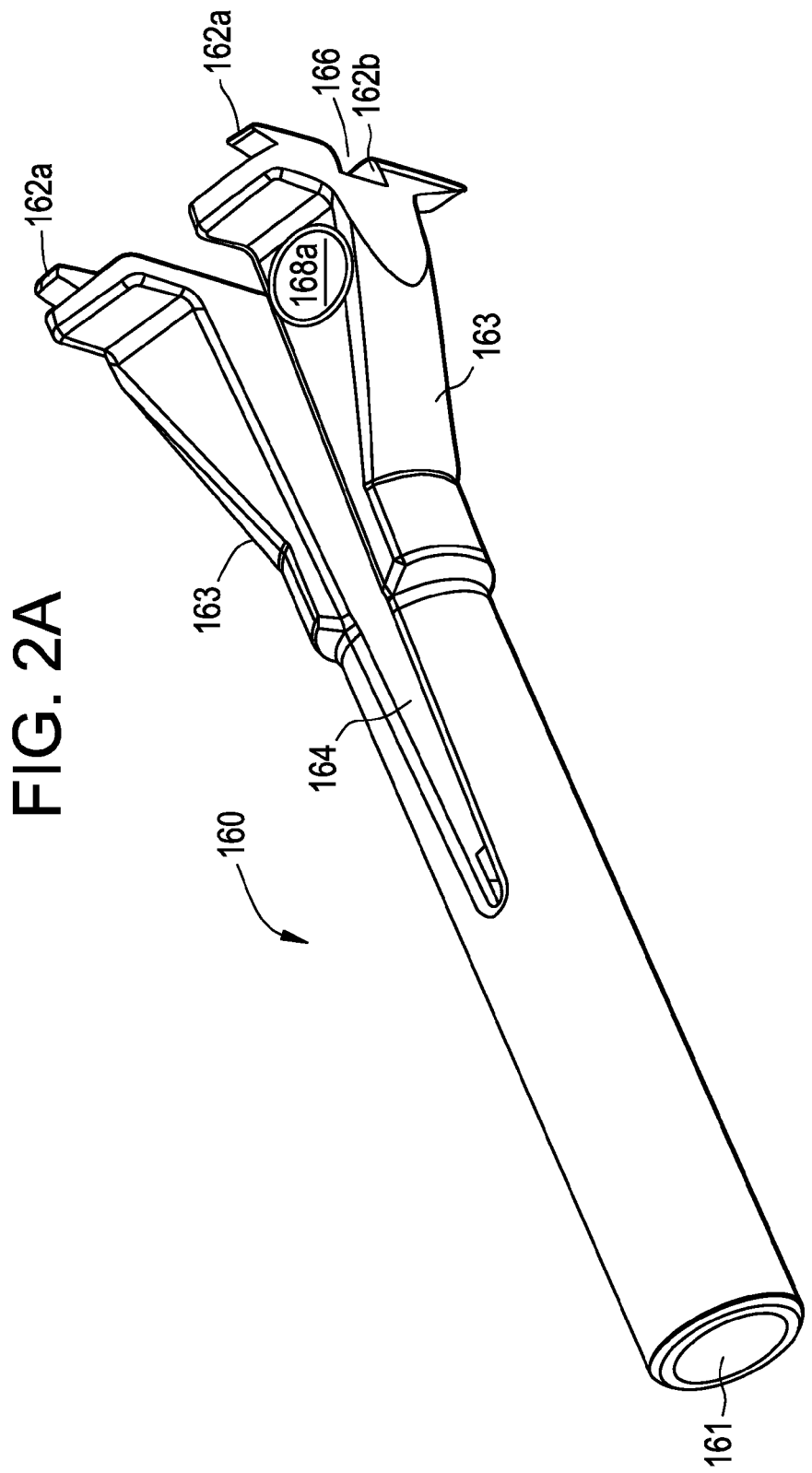

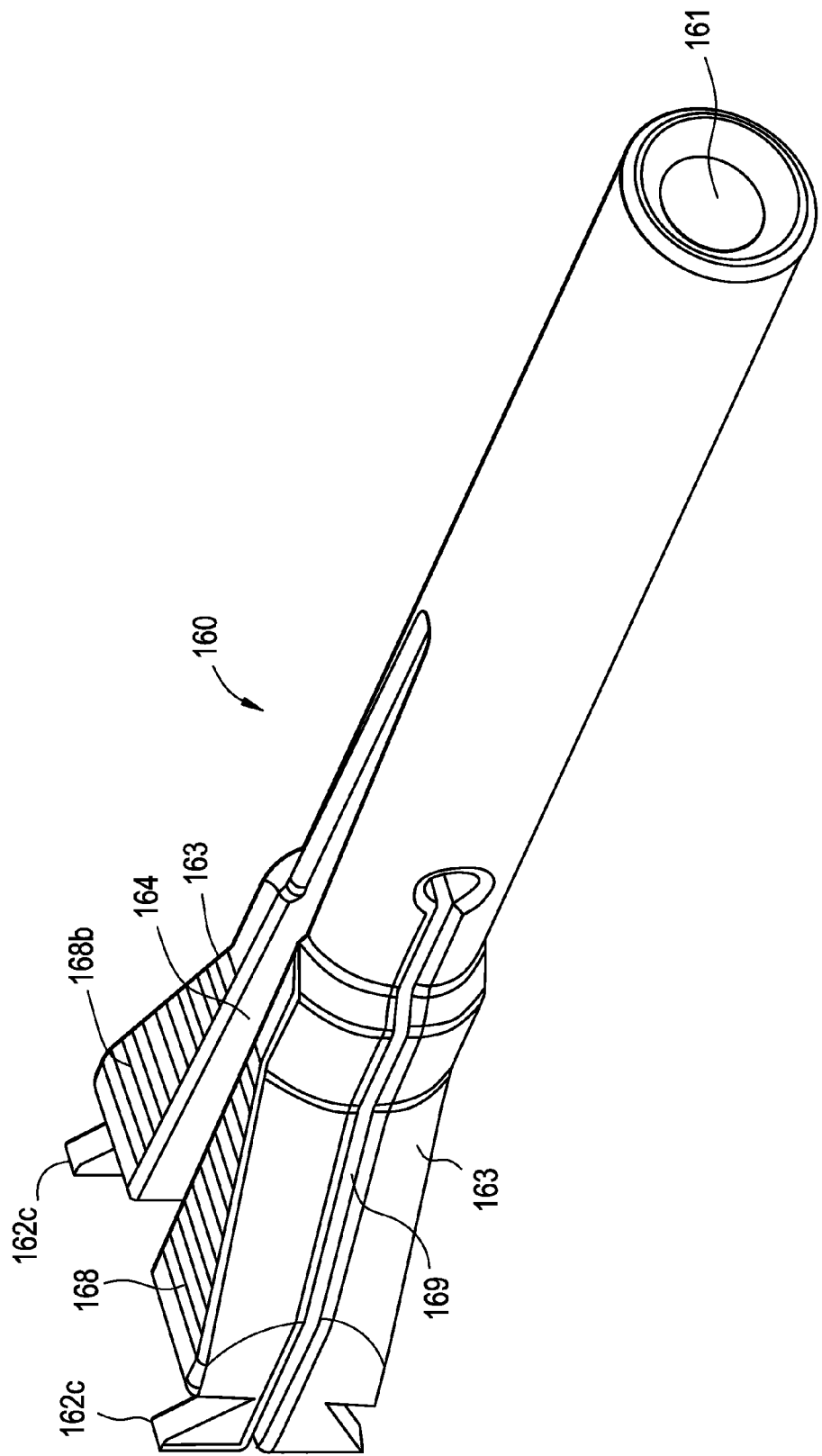

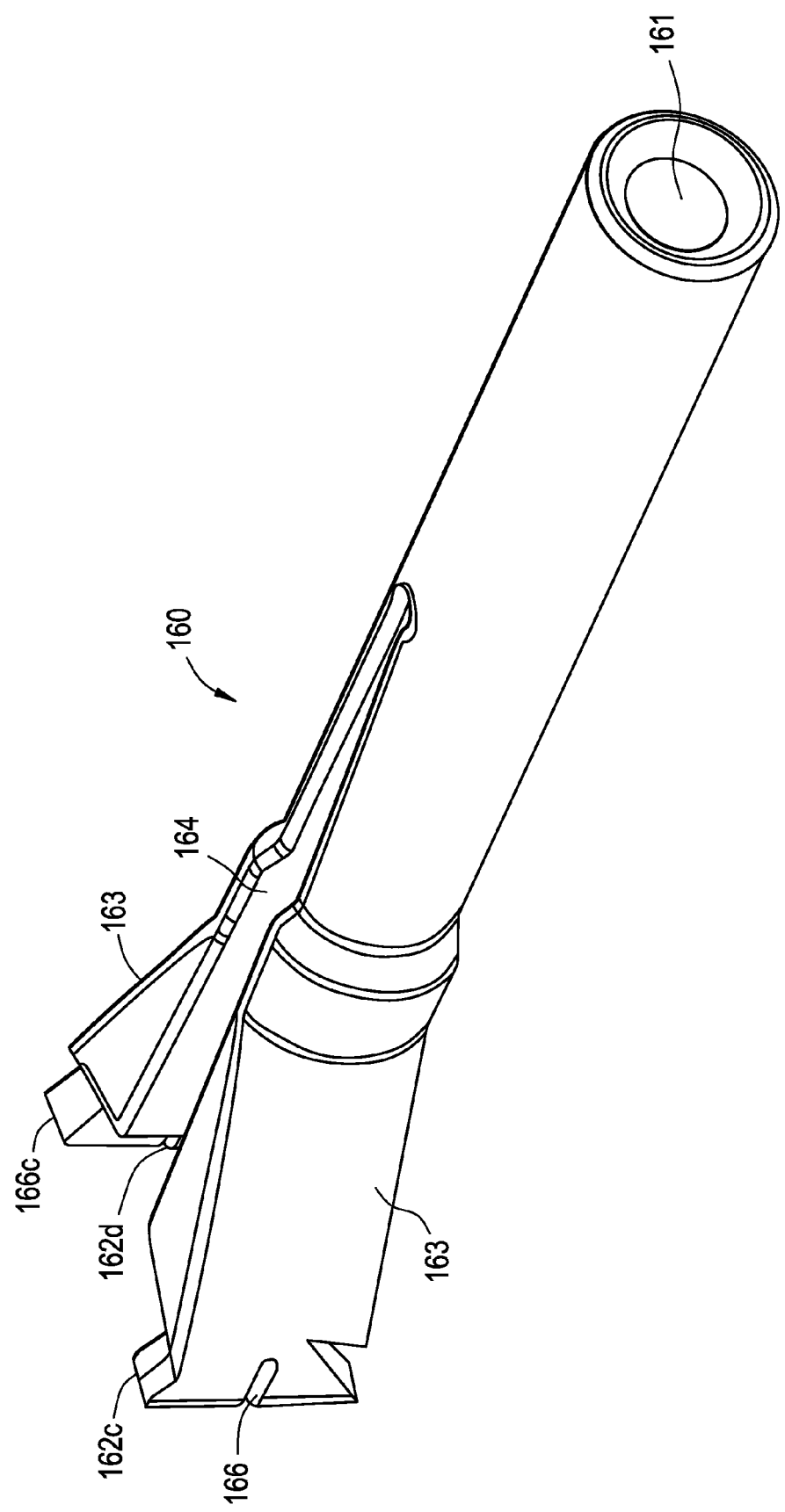

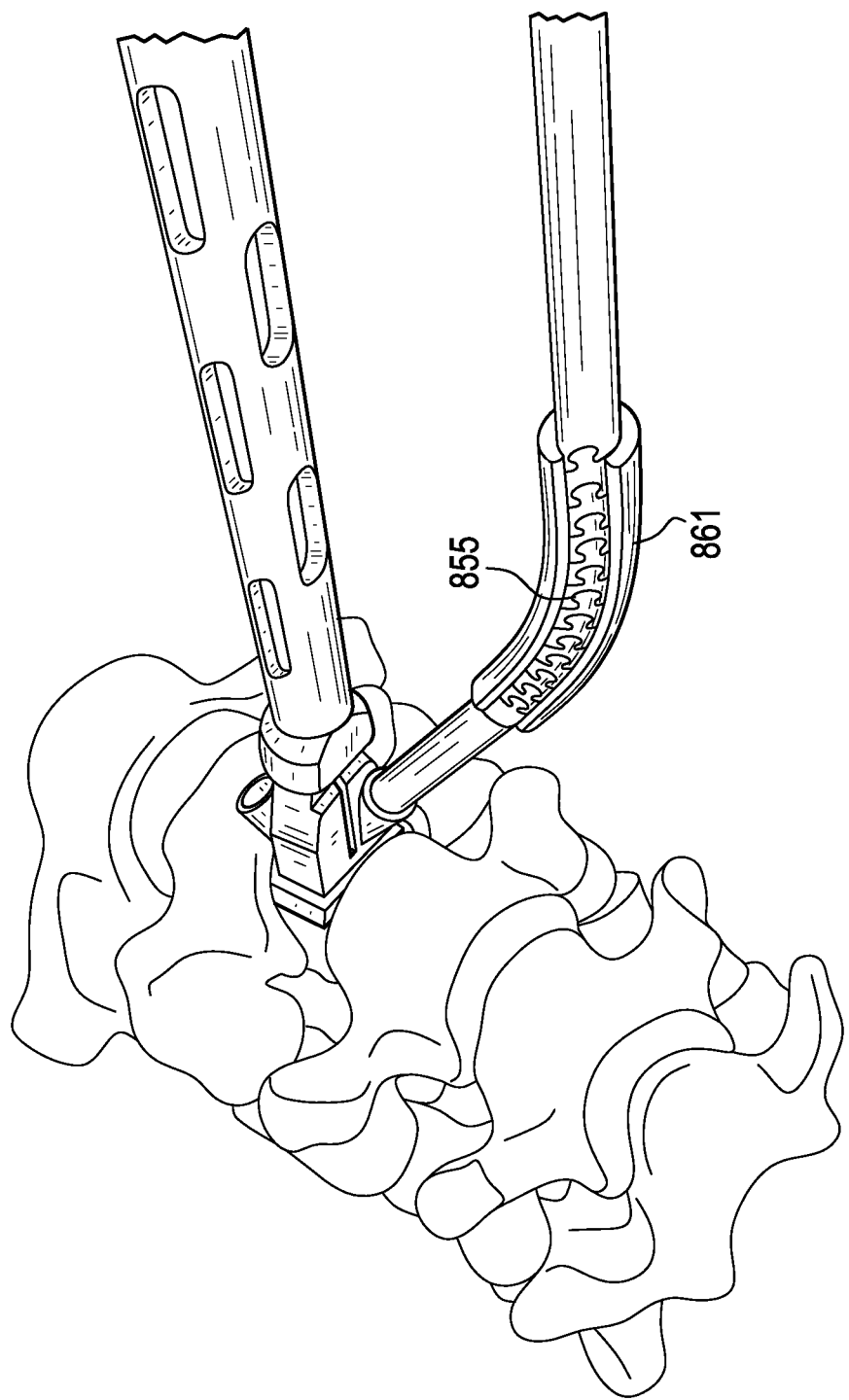

IMPLANT INSERTER HAVING A LATERALLY-EXTENDING DOVETAIL ENGAGEMENT FEATURE

CONTINUING DATA

This application claims priority from U.S. Ser. No. 61/385,959, filed on Sep. 23, 2010, and entitled "Stand Alone Intervertebral Fusion Device ", and is related to non-provisional U.S. Ser. No. 13/237,233, filed on Sep. 20, 2011, entitled "Stand Alone Intervertebral Fusion Device", the specifications of which are incorporated by reference in their entireties.

This application claims priority from U.S. Ser. No. 61/466,309, filed on Mar. 22, 2011, and entitled "Novel Implant Inserter Having a Laterally-Extending Dovetail Engagement Feature", and from U.S. Ser. No. 13/237,200, filed on Sep. 20, 2011, and entitled "Novel Implant Inserter Having a Laterally-Extending Dovetail Engagement Feature", the specifications of which are incorporated by reference in their entireties.

This application claims priority from U.S. Ser. No. 61/466,321, filed on Mar. 22, 2011, and entitled "Fusion Cage with In-Line Single Piece Fixation", and is related to non-provisional U.S. Ser. No. 13/237,174, filed on Sep. 20, 2011, entitled "Fusion Cage with In-Line Single Piece Fixation", the specifications of which are incorporated by reference in their entireties.

BACKGROUND OF THE INVENTION

Spine surgeons have expressed a desire to locate an implant with a low vertical profile instrument to minimize retraction and increase visibility of the implant. Ideally, the instrument and its connection point are sized to be fully contained within the profile of the implant, thus being smaller than the implant and allowing easy positioning or placement of the implant. Additionally, the connection to the instrument should be desirably rigid, with no toggle or rotation in any plane. This rigidity prevents implant movement during the passing of instruments or bone screw insertion.

Conventional inserter instruments possessing chamfer features typically work in one plane, wherein a grabber tip collapses upon the implant in a medial/lateral direction and thereby secures the implant to the instrument. However, even with exacting tolerances, toggle often appears if the user of the conventional instrument were to apply a moment to the posterior edge of the implant (in flexion/extension) in one plane. Conventional inserters with chamfer features also do not take advantage of dissimilar angles at the interface in more than one plane, and so fail to ensure that the anterior surface of the implant bottoms out on the inserter grabber tip.

U.S. Pat. No. 5,443,514 (Steffee) discloses an inserter that grips the side of a spinal implant. See FIGS. 4-6 of Steffee.

US Patent Publication No. 2005-0143749 (Zalenski) discloses an inserter having engagement features forming a vertically-extending dovetail shape. See FIGS. 2A-2C of Zalenski.

SUMMARY OF THE INVENTION

The present invention relates to an intervertebral implant having a novel "compound angle" recess, such as a dovetail shape, designed and sized to couple to a delivery instrument. The interface between the implant and securing instrument is designed with laterally-extending, angled chamfer features extending in more than one direction to prevent toggle and rotation. Once the split tip instrument is collapsed to its closed position, the implant is drawn into the inserter and allowed to bottom out on a distal wall of the inserter.

The instrument of the present invention is advantageous over conventional inserter instruments having threads and other known grabber features, which sometimes need to withstand impaction and may move upon insertion of a bone anchor or instruments through the device.

The dual angle nature of the present invention ensures that the implant is axially square and/or co-linear with the instrument and so further ensures that a larger surface area of the instrument absorbs any required impaction.

The present invention may also have an added angle, wherein the dimension on the anterior portion of the feature is sized to be smaller than the posterior portion of the feature. See FIG. 6.

In particular embodiments, the instrument of the present invention has a forked inner shaft with distal tynes extending therefrom, wherein each distal tyne forms a medially-extending dovetail feature. This dovetail feature possesses the compound angulation that prevents the undesired movements discussed above.

In preferred embodiments of the present invention, the proximal wall of the implant has a corresponding pair of recesses opening onto its respective lateral walls. Each of these recesses forms a dovetail silhouette on its respective lateral wall of the implant.

The invention is generally related to a method and apparatus for assisting in a safe, one-handed insertion of an implant. The implant implantation device generally includes (i) a frame that includes a trigger mechanism, (ii) an outer sleeve mechanically coupled to the frame, (iii) a forked inner shaft having distal tynes for mechanically engaging an implant, the forked inner shaft slidably disposed within the outer sleeve and (iv) a retaining element for directing the distal tynes towards a closed position. The retaining element can be a spring.

Optional elements on the inserter may include a knob, a drag adjustment screw, at least one protrusion, and a depth control member. The knob can be mechanically coupled to the outer sleeve for causing the outer sleeve and the forked inner shaft to be rotated about the frame. The drag adjustment screw can provide tension between the trigger mechanism and the forked inner shaft. The at least one protrusion can be located on the outer sleeve for slidably engaging a distraction instrument. The depth control member can be slidably coupled to the outer sleeve for providing a predetermined insertion depth of the implant.

The distal tynes of the inserter hold the implant therebetween during insertion of the implant between the vertebrae. Each distal tyne includes an engagement feature at its tip for mechanically engaging the implant. The engagement feature comprises a dovetail-shaped protrusion extending in the lateral direction. Generally, the engagement feature has a medial face, with each medial face having a proximal end portion having a height and a distal end portion having a height, wherein the height of the distal end portion is greater than the height of the proximal end portion. At the same time, the front wall of the implant comprises a pair of mating laterally-extending dovetail recesses opening onto a respective side wall and forming a dovetail silhouette on each side wall, wherein each engagement feature of the instrument is received in a respective recess of the spinal implant.

The forked inner shaft can include at least one marking to identify a position of the implant in relation to the patient.

The marking can be a pin located on a surface of the forked inner shaft. The marking can be a plurality of machined slots on a surface of the forked inner shaft.

Mechanically engaging the implantation instrument to the implant may include the steps of (i) opening the forked inner shaft located on an end of the implantation instrument, (ii) aligning the tynes of the forked inner shaft with the recesses of the implant, and (iii) closing the tynes to mechanically engage the tynes to the implant.

The method may further include the steps of (iv) distracting a prepared disc space with a distraction instrument, (v) inserting the implant into the prepared disc space with the implantation instrument, (vi) releasing the implant from the implantation instrument, and (vii) removing the implantation instrument and distraction instrument.

In some embodiments, inserting the implant into a prepared disc space may include the step of aligning the implantation instrument with the distraction instrument.

The invention has many advantages. For example, the invention provides safe one-handed insertion of an implant into a prepared disc space. The invention reduces the amount of time required to complete the surgical procedure. The invention also provides for various manipulations of the implant without physically contacting the implant. For example, the invention can align an endplate of the implant radially and provide a lordotic angle for implantation. The invention can be used for packaging the implant, and the invention can be used to hold the implant during the implant sterilization process.

Therefore, in accordance with the present invention there is provided an instrument for inserting an implant, comprising;
 a) an outer sleeve having a bore, and
 b) a forked member having a proximal rod and a pair of distal tynes extending therefrom, each distal tyne comprising a proximal portion and a distal portion having a distal wall having an engagement member extending distally therefrom, each engagement member having a medial face forming a dovetail shape,
wherein the proximal rod and the proximal portion of each tyne are slidably received within the bore of the outer sleeve, and
wherein the distal portion of each tyne extends out of the bore of the outer sleeve.

Also in accordance with the present invention there is provided an assembly comprising:
 a) the above-described inserter, and
 b) a spinal implant having a front wall, a pair of opposing side walls and a back wall,
  wherein the front wall comprises a pair of recesses opening onto a respective side wall to form a dovetail shape in each respective side wall,
 wherein each engagement feature of the instrument is received in a respective recess of the spinal implant.

Also in accordance with the present invention there is provided an orthopedic implant having a front wall, a pair of opposing side walls, a back wall, and top and bottom surfaces, wherein the front wall comprises a pair of recesses, each recess opening onto a respective side wall and forming a dovetail shape in the respective side wall.

DESCRIPTION OF THE DRAWINGS

FIG. 1A shows a cross-sectional view of an insertion instrument of the present invention.

FIGS. 2A-2C show a perspective view of three embodiments of a forked inner shaft of the present invention.

FIGS. 8A-8F disclose a flexible screw inserter and a prebent sleeve.

DETAILED DESCRIPTION OF THE INVENTION

Figure 1B:
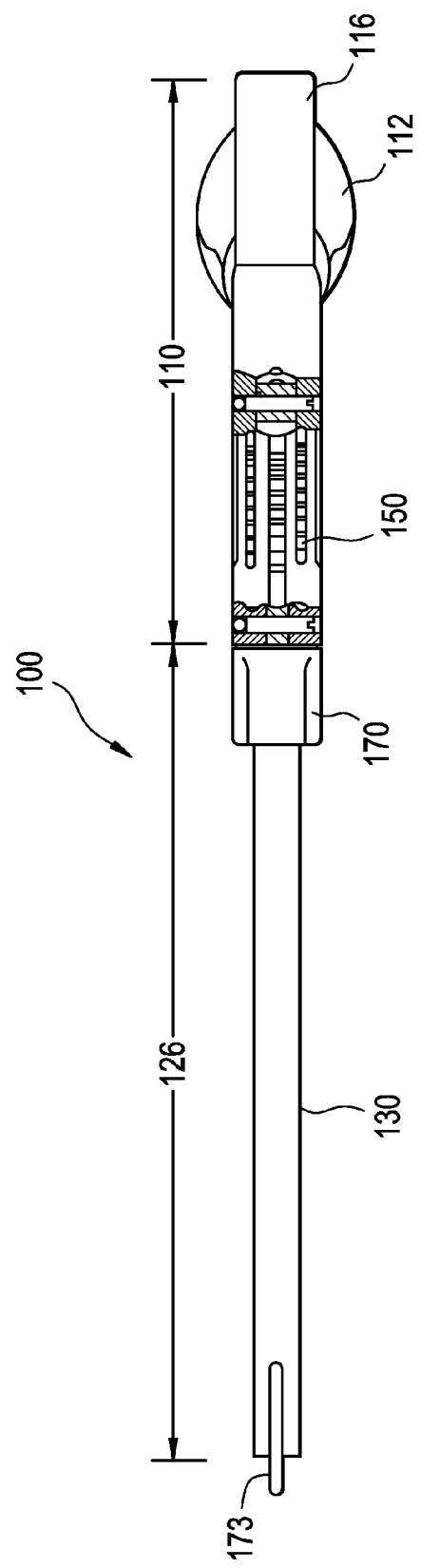
FIG. 1B shows a plan view of the insertion instrument of FIG. 1A.

The foregoing and other objects, features and advantages of the invention will be apparent from the following more particular description of preferred embodiments of the invention, as illustrated in the accompanying drawings in which like reference characters refer to the same parts throughout the different views. The same number appearing in different drawings represents the same item. The drawings are not necessarily to scale, with emphasis instead being placed upon illustrating the principles of the invention.

In general, the present invention is related to an apparatus and a method for safely inserting an implant into a spine. The implant can be an artificial disc or spinal fusion cage, or a spinal plate. Referring to FIGS. 1A and 1B, insertion instrument 100 is shown in a side cross-sectional view and a plan view, respectively. Insertion instrument 100 includes a frame or driver body assembly 110, an actuator assembly 126 and a forked inner shaft 160 (FIG. 2A-2C). Insertion instrument 100 is a normally closed device, that is, the proximal rod of the forked inner shaft 160 is normally substantially contained within actuator assembly 126.

Figure 3:
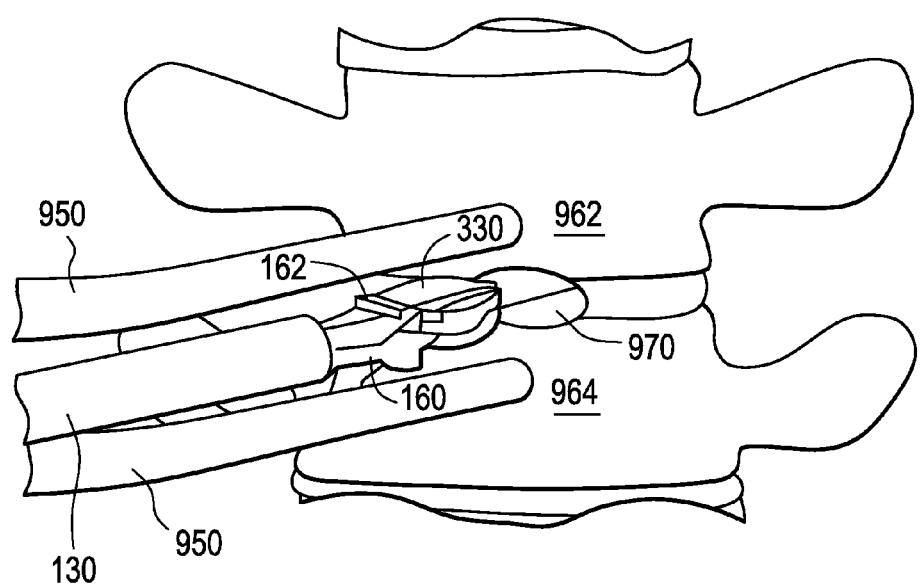
FIG. 3 shows a perspective view of the implant being inserted into a prepared disc space using the insertion instrument of FIGS. 1A-2C.

Actuator assembly 126 includes an outer sleeve 130, a proximal inner shaft 140, and a retaining pin 148. Outer sleeve 130 includes a tapered end 175 which slidably engages tapers 163 on the forked inner shaft 160 (FIG. 2A-2C), allowing for compression and expansion of the forked inner shaft 160 when in use. Inner shaft 140 includes a female threaded end 142 and a male threaded end 144. Female threaded end 142 mates with a spring retaining screw 152 and male threaded end 144 mates with the forked inner shaft 160. Internal compression spring 150 is fastened to the actuator assembly 126 and is held in place by spring retaining screw 152. Once actuator assembly 126 is assembled, it is inserted into driver body assembly 110 and retained within assembly 110 with retaining pin 148. Optional knob 170 can be mechanically attached to outer sleeve 130 to allow outer sleeve 130 and proximal inner shaft 140 to rotate about the driver body assembly 110. Optional guides 171 can be attached to outer sleeve 130 to slidably mate with spinal disc distraction instrument 950 (FIG. 3). Depth control member 173 can also be fixedly or slidably attached on outer sleeve 130 for providing a predetermined insertion depth of the implant.

Driver body assembly 110 includes handle 112, handle transition 114, strike boss 116, trigger mechanism 120, and pivot pin 122. Trigger mechanism 120 can be any type of trigger mechanism known in the art. Trigger mechanism 120 pivots about pivot pin 122 in the driver body assembly 110. When trigger mechanism 120 is squeezed toward handle 112, the forked inner shaft 160 (FIG. 2A-2C) extends from actuator assembly 126 and expands to release an implant. When trigger mechanism 120 is released, forked inner shaft 160 recedes into actuator assembly 126 and compresses, thereby engaging the implant or returning to its normally closed position. Optional drag adjustment screw 124 is rotatably coupled to driver body assembly 110 for adjusting the drag force between trigger mechanism 120 and spring retaining screw 152 of actuator assembly 126.

FIGS. 2A-2C show various forked inner shafts 160 of the present invention. Each forked inner shaft 160 includes engagement features 162 for mechanically engaging the implant. engagement features 162 may be various shapes and sizes depending upon implant selection. As shown, engagement features 162 may be dovetail-shaped (162a, 162b, 162c, 162d). Engagement features 162 can engage implants having multiple heights. It should be understood engagement features 162 can be any shape which can engage any type of implant. In an alternative embodiment, proximal inner shaft 140 and forked inner shaft 160 can be integral.

Each forked inner shaft 160 includes female threaded hole 161 for mating to male threaded end 144 of proximal inner shaft 140 of actuator assembly 126. It should be understood that any means known in the art can be used to attach forked inner shaft 160 to proximal inner shaft 140.

Each forked inner shaft 160 includes tapers 163 and relatively long expansion/compression slot 164 to allow forked inner shaft 160 to expand and compress during use. FIGS. 2A-2C show forked inner shaft 160 in the expanded position. Each forked inner shaft 160 also includes sizing slot 166 to allow for a variation of tab and forked inner shaft slot dimensional differences. Expansion/compression slot 169 (FIG. 2B) is an alternative embodiment of sizing slot 166. In some embodiments, the forked member has a quick connect feature.

Cephalad markers 168 can be included on a surface of forked inner shaft 160 to allow the user to determine the position of the implant. Markers 168 can be pin 168a or machined slots 168b. In some embodiments, the inserter (squeeze handle) has a quick connect feature.

Figure 4A:
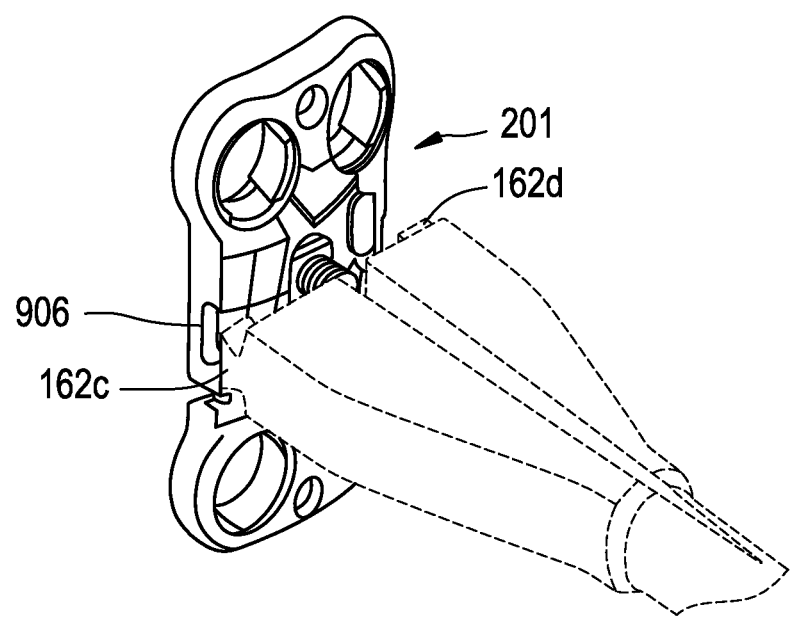
FIG. 4 show two views of an instrument of the present invention having dovetail gripping features approaching an implant having corresponding dovetail recess features.
Figure 4B:
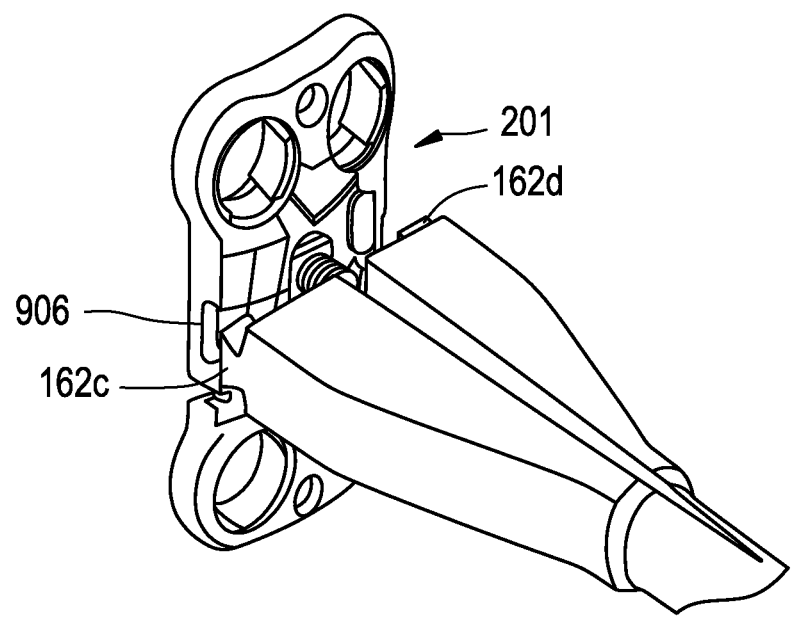

In one method of using the present invention, and now referring to FIGS. 4a and 4b, the user first squeezes the trigger mechanism 120 (FIG. 1) on the implantation instrument 100, thereby causing the engagement features 162c, 162d on the instrument to separate. The user then approaches the target implant (in this case, a cervical plate 201) with the implantation instrument so that the dovetail features of these two devices align, whereby the engagement features 162 straddle the opposed engagement indents 906 on the implant. Once engagement features 162 straddle the engagement indents 906, the user then releases the trigger mechanism 120, causing engagement features 162 to collapse inwards and engage engagement indents 906 on the implant.

In other embodiments, the reverse is provided, wherein the user squeezes the instrument to engage the implant.

Figure 5:
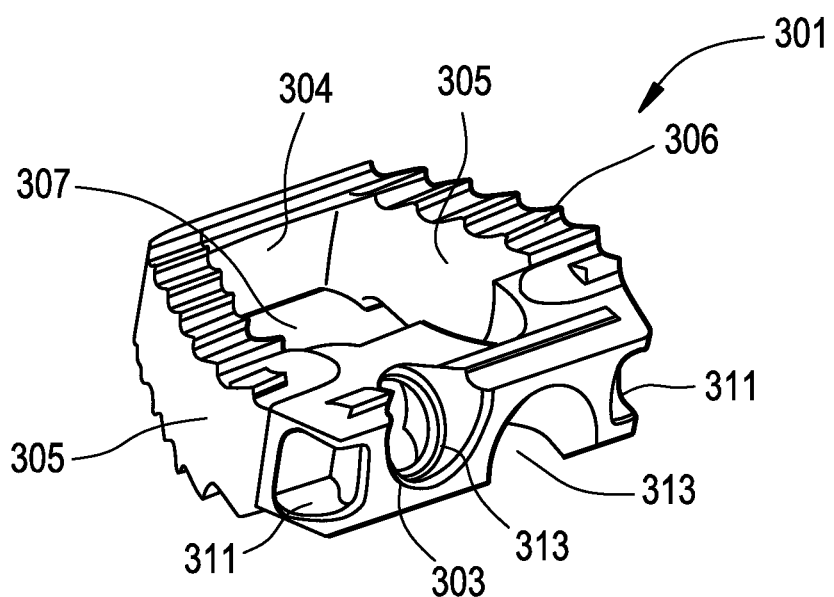
FIG. 5 discloses an intervertebral fusion cage of the present invention.

Now referring to FIG. 5, there is provided an intervertebral fusion cage 301 of the present invention. This cage comprises a front wall 303, a back wall 304, a pair of opposing side walls 305 connecting the front and back walls, a top surface 306 adapted to engage an upper vertebra, a bottom surface (not shown) adapted to engage a lower vertebra, and a throughhole 307 extending between the top and bottom surfaces for promoting fusion therethrough, wherein the front wall comprises a pair of recesses 311, each recess opening onto a respective sidewall and forming a dovetail shape in the respective sidewall. The front wall of this particular cage also has screwholes 313 extending therethrough. The screwholes are typically threaded and are adapted to receive bone screws for securing the cage to opposing vertebral bodies without the need for posterior instrumentation, thereby providing "stand alone" capabilities.

Figure 6:
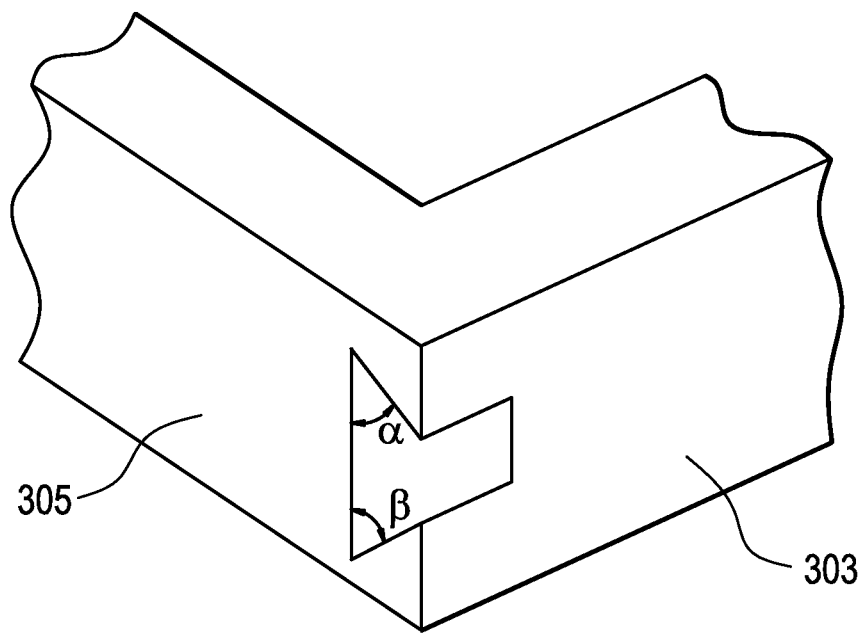
FIG. 6 discloses a corner of an implant having a sidewall having recess therein, wherein the recess comprises two acute angles α and β.

Now referring to FIG. 6, also in accordance with the present invention, there is provided a spinal implant having a front wall, a pair of opposing side walls, a back wall, and top and bottom surfaces, wherein the front wall comprises a pair of recesses, each recess opening onto a respective side wall and forming at least two acute angles $\alpha$ and $\beta$ in the respective side wall. The acute nature of these two angles in the same recess creates the condition necessary to preclude toggle and rotation.

In some embodiments, the top and bottom surfaces of the implant are spaced at a distance suitable for contacting opposing vertebral endplates. This feature is advantageous for spinal implants inserted into a disc space.

In some embodiments, the implant of the present invention has a throughhole extending from its top surface to its bottom surface. This throughhole feature promotes bony fusion through the implant and so provides a performance advantage for fusion cage embodiments of the present invention.

In some embodiments thereof, a bone graft material is contained in the throughhole of the fusion cage. This graft material also promotes fusion through the implant and so provides a performance advantage for fusion cage embodiments of the present invention.

In some implant embodiments, the fusion cage has a front wall that is manufactured separately from the remainder of the implant. Preferably, the front wall is metallic and the remainder of the implant is polymeric. This preferred embodiment advantageously provides strength in the front wall so that screw holes can pass therethrough without fracturing the wall.

In some embodiments, first and second bone fasteners extend through the screwholes located in the front wall of the fusion cage. This feature allows the cage to be secured to the opposing vertebrae and so eliminates the need for posterior instrumentation. In some embodiments thereof, the first fastener further extends through the top surface of the implant, while the second fastener further extends through the bottom surface of the implant.

In some embodiments, the first and second bone fasteners extend only through the front wall, as in a plate embodiment.

In some embodiments, the implant has an articulation interface, as in an articulating motion disc.

FIG. 3 discloses an instrument of the present invention inserting an implant of the present invention into a disc space.

As shown in FIG. 3, distraction instrument 950 is inserted over pins (not shown) that are secured into vertebral bodies 962, 964. Cervical fusion cage 330 is passed between the forks of distraction instrument 950 using implantation instrument 100 (FIGS. 1A-1B). In an alternate embodiment, guides 170 on insertion instrument 100 slidably engage slots in the forks of distraction instrument 950 to help the user guide cervical fusion cage 330 into prepared disc space 970.

Once the cervical fusion cage 330 is in a desired location within prepared disc space 970, the user actuates (e.g., squeezes, or releases or rotates a knob) trigger mechanism 120 (FIG. 1A), which releases cervical fusion cage 330 into the prepared disc space 970. The user can determine the desired position by observing cephalad markers 168 (FIGS. 3A-3B) located on a surface of forked inner shaft 160. In an alternative embodiment, implantation instrument 100 can include a depth control member 173 (FIG. 1A) (which might be an adjustable and slidable), such that cervical fusion cage 330 can be inserted into prepared disc space 970 at a predetermined depth.

Lastly, the implantation instrument 100 and distraction instrument 950 are removed, causing superior vertebra 962 and inferior vertebra 964 to engage cervical fusion cage 330.

Figure 7:
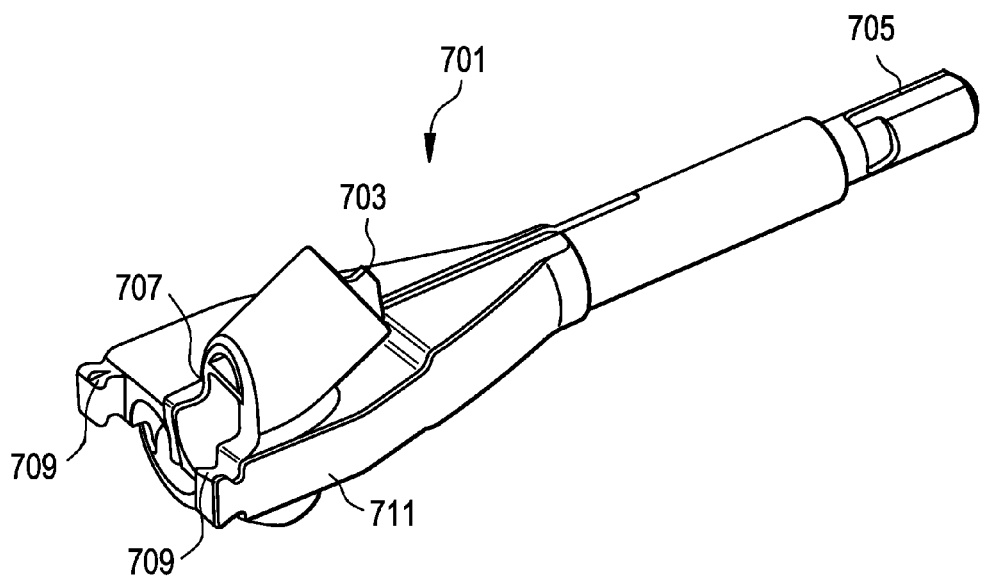
FIG. 7 discloses a perspective view of an inserter tip of the present invention.

Now referring to FIG. 7, there is provided one embodiment of an inserter tip 701 of the present invention. This inserter tip includes barrel stop 703 that prevents the bone screw from stripping. There is a distal quick connect/release feature 705 that allows for ease of connection to the remainder of the inserter instrument. Barrels 707 prevent the implant from being placed too far posteiorly. Relief features 709 on the dovetail allow for the engagement feature to disengage with ease from the implant. Lastly, barrels 711 can be a fixed barrel or adjustable via sliding member such as a ratcheting feature.

Figure 8:
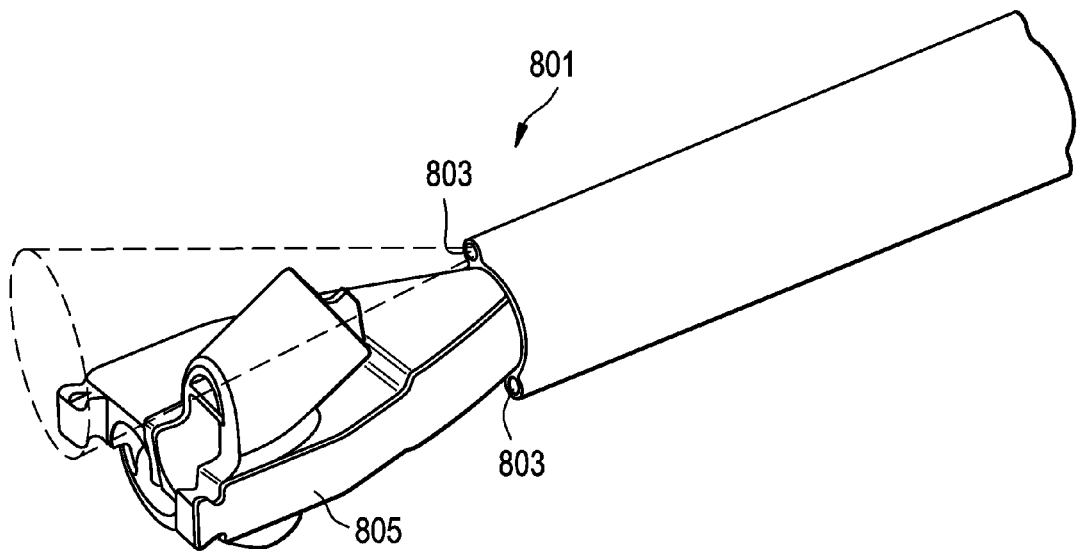
FIG. 8 discloses a perspective view of a lighted inserter tip of the present invention.
Figure 8A:
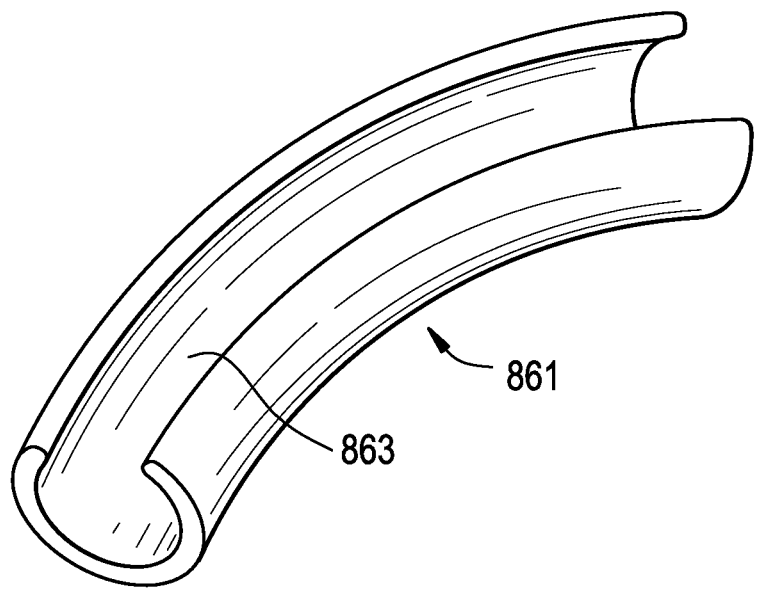
Figure 8B:
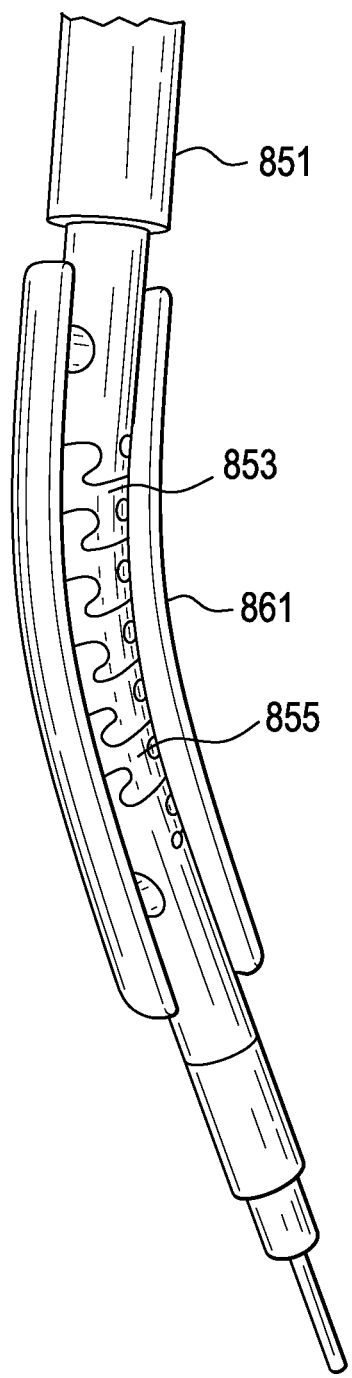
Figure 8C:
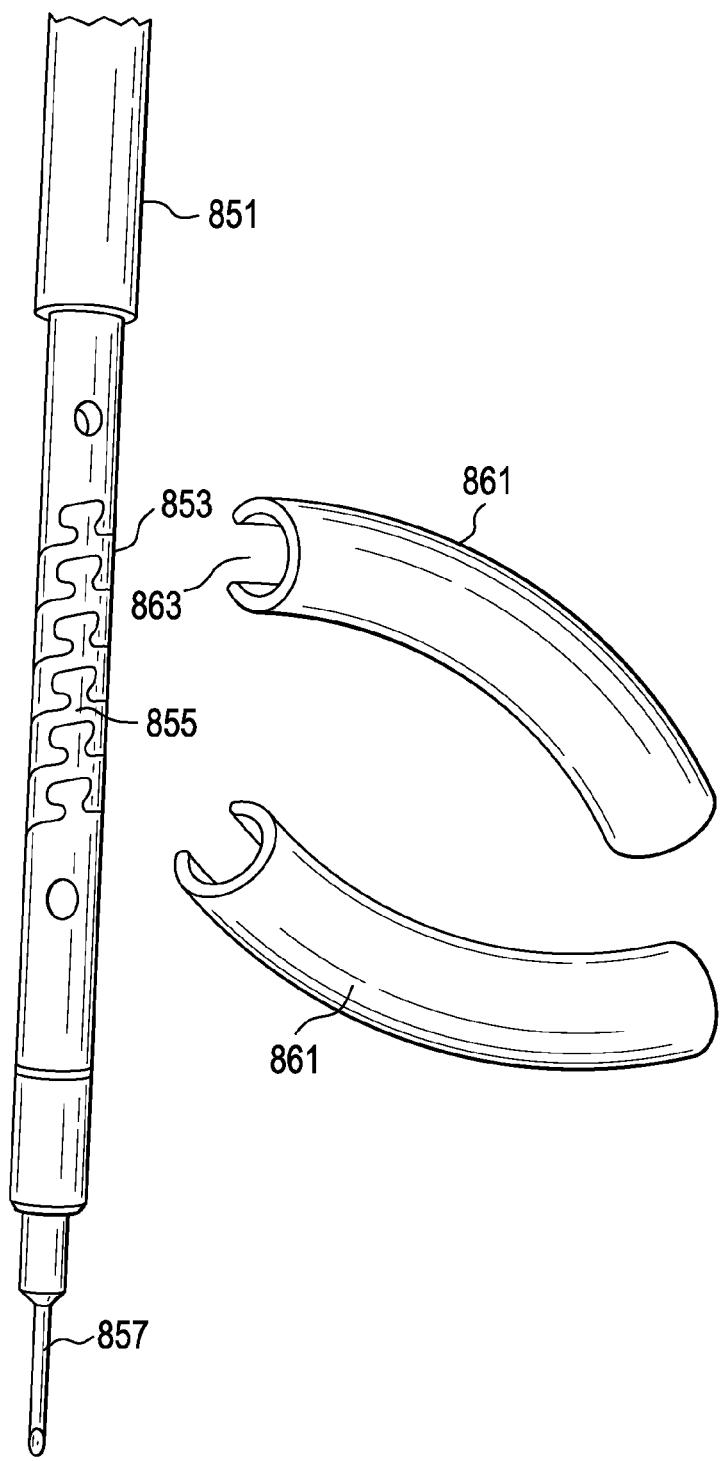
Figure 8D:
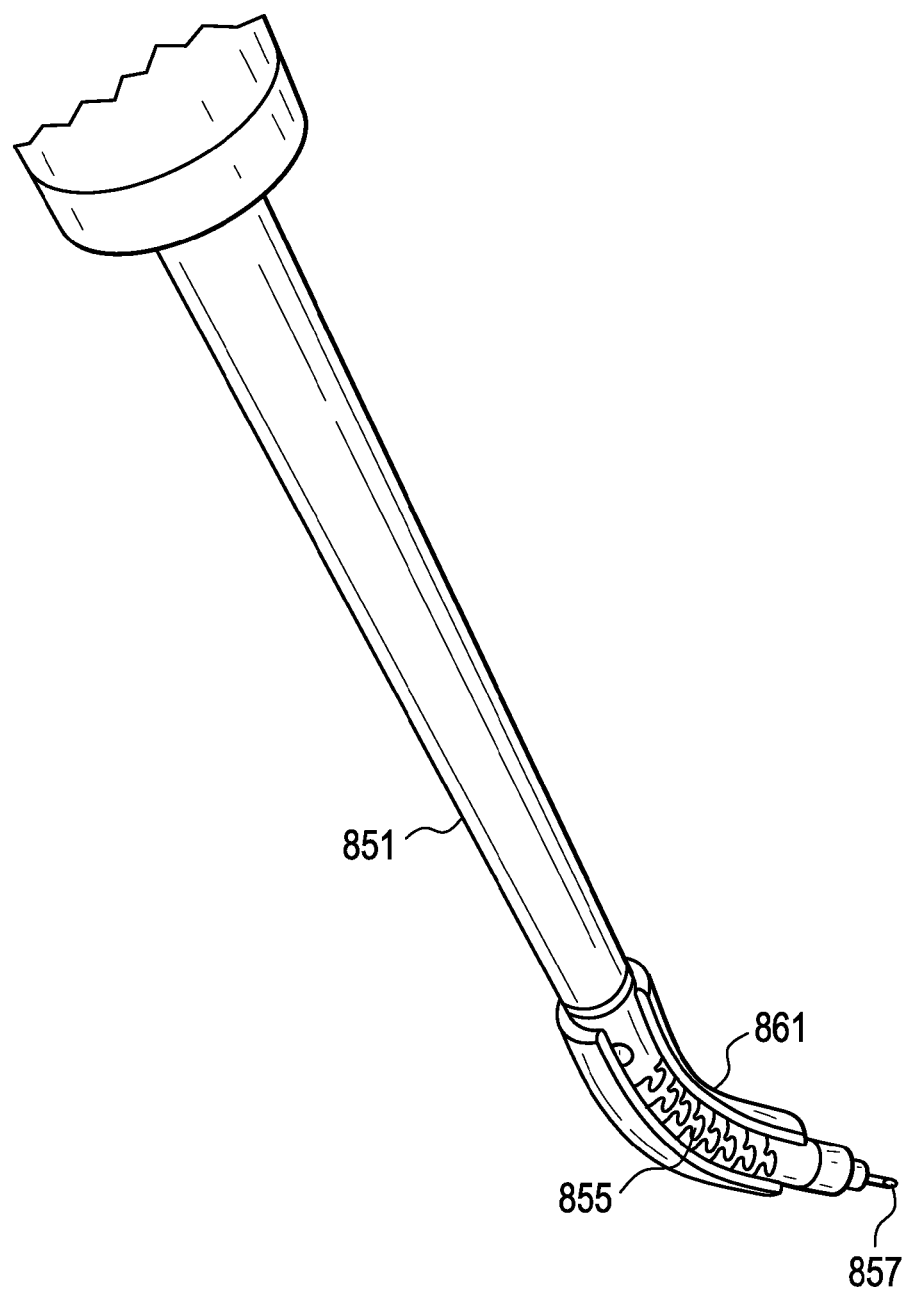
Figure 8F:
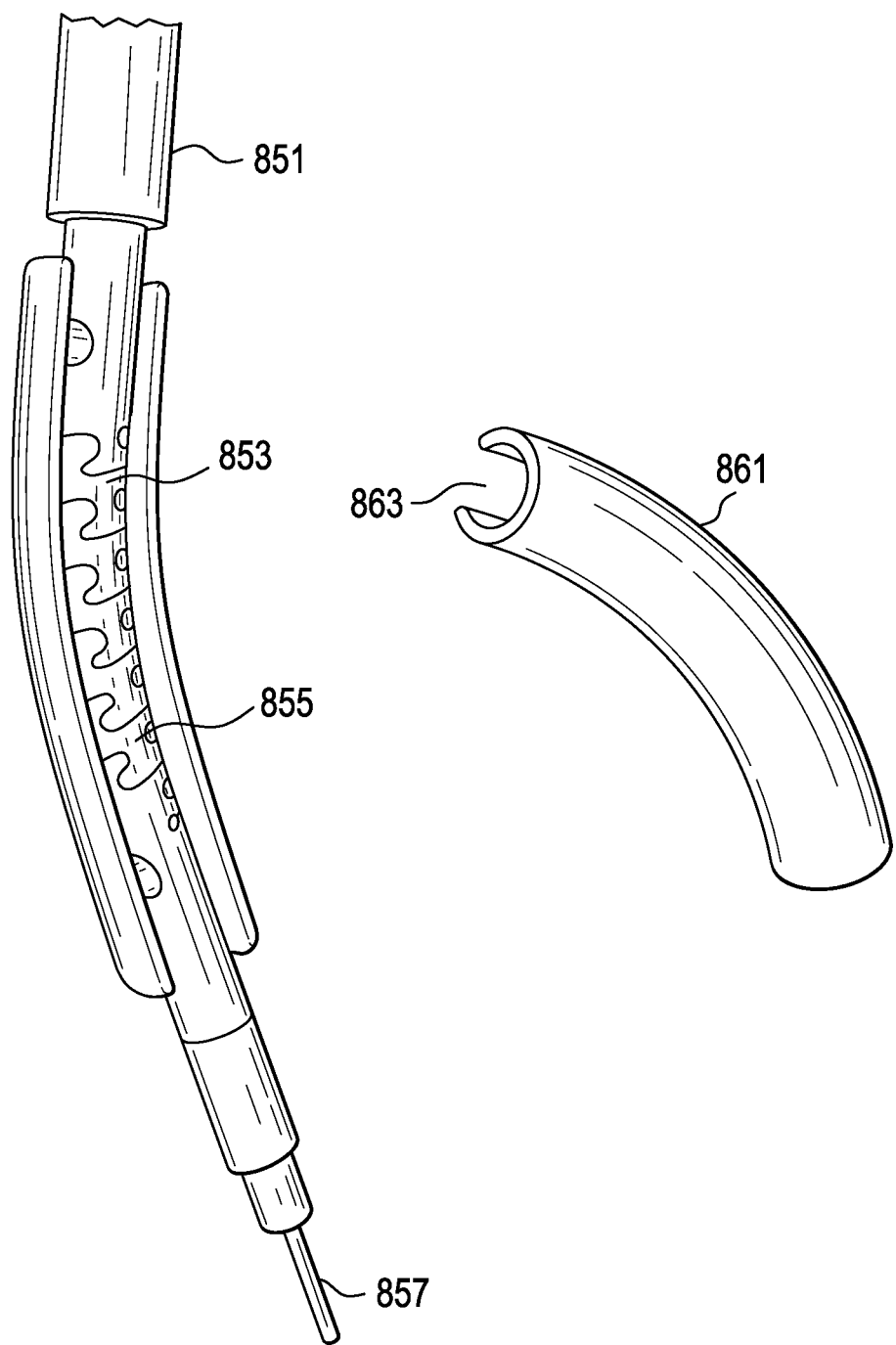

Now referring to FIG. 8, there is provided one embodiment of a lighted inserter tip 801 of the present invention. The inserter cannula is fitted with at least one secondary lumen 803 adapted for delivering light or delivering a fiber optic. Light emanating from the secondary lumen is shown by the dashed lines in FIG. 8. Alternatively, light can be fed down the major lumen that holds the inserter tip (not shown). In one embodiment, at least the engagement features 805 of the tip are made of hard clear plastic that allows visibility of the other instruments passed through the barrels.

When performing a spinal procedure such as an anterior cervical discectomy and fusion (ACDF), the surgeon often has a number of implant options that may achieve the desired clinical outcomes of disc height maintenance and pain relief. Because of their clinical benefits, zero-profile fusion cages that accept bone anchors and are secured to the adjacent anatomy have experienced an increased usage and adoption in the ACDF procedure. These cages typically have angled bone anchors (such as screws) that pass through a portion of the cage's anterior wall and into the adjacent vertebral endplates.

However, if a surgeon were to choose a low profile, stand-alone fusion device (such as a fixation cage comprising one or more bone screws), there remains a surgical technique challenge associated with the insertion of the screws. Traditionally, an instrument having a straight shaft is used to insert the screws through the cage at the steep angle to ensure bone penetration. However, screw insertion with a straight-shaft instrument at locations up near a patient's chin or sternum produces some challenging approach angles. Recently, there have been improvements to the insertion instrument that help facilitate screw placement at these difficult approach angles. Some of these improvements include the adoption of universal joints and flexible inserter instruments that allow for torque transmission while still positioning their handles off-axis from the trajectory of the screw. For example, some flexible inserter instruments achieve flexibility by possessing a plurality of interlocking segments just proximal of their distal working tip. Once the tip of such a flexible driver is inserted into the drill guide, the handle of the driver can be repositioned to the desired location and torque can be transmitted to advance the screw.

However, one of the challenges associated with this flexible technology is that the flexible shaft is typically straight in its resting configuration. Accordingly, one of two procedures needs to be carried out. In a first procedure, the amount of soft tissue retraction has to temporarily be increased in order to engage the tip of the driver into the drill guide and once engaged, the soft tissue retraction can be minimized again and the handle can be held in a desirable position, such as near parallel to the implant inserter. In a second procedure, the tip can be inserted into the drill guide at a less steep angle than the screw trajectory (but not perfectly parallel to the inserter) and the spring force of the flex segment has to be overcome in order for the tip to find the drill guide trajectory. Upon this "turning the corner" step, as a downforce is provided, the self-retention of the screw may become disengaged.

Therefore, to overcome these issues, in one aspect of the present invention, and now referring to FIGS. 8A-8F, there is provided an improvement on the flexible shaft technology that has benefits for the patient and the surgeon. The improvement is a bone screw driver having a) a proximal handle (not shown), b) an intermediate shaft 851, c) a flexible distal end portion 853 comprising a plurality of interlocking segments 855 and distal tip 857 (wherein the flexible distal end portion is substantially straight in its unloaded configuration), and d) a pre-bent sleeve 861 that is placed over and around the flexible segments, thereby pre-determining the trajectory of the tip and facilitating the appropriate and desired insertion angle of the screw into the drill guide without increasing the amount of refraction. As shown in FIGS. 8a-8f, this pre-bent sleeve (which has a longitudinal slit 863) allows a screwdriver handle to be perfectly in-line with the cage inserter if desired, while still taking advantage of the tactile feel and torque transmission of the flex segment in its bent position. Accordingly, a surgeon can limit the amount of retraction and keep the driver handle close to the inserter without having to overcome the forces of the flexible segments' natural straight configuration. The sleeve can be fixed, slidable, or removable and can fully or partially encompass the flexible segments. The sleeve can have geometries that allow for flexing, attachment (snapping-on) to the driver, and removal for cleaning, if desired. The sleeve can be made of any biocompatible material that will maintain the desired shape (such as metal or plastic).

Therefore, in accordance with the present invention, there is provided a flexible bone screw driver comprising:
  a) a proximal handle,
  b) an intermediate shaft,
  c) a flexible distal end portion comprising a plurality of interlocking segments and a distal tip adapted to engage a screw head, and
  d) a pre-bent sleeve placed over and around the plurality of interlocking segments.

Also in accordance with the present invention, there is provided an assembly comprising:
  a) a fusion cage comprising a front wall, a pair of opposing side walls, a back wall, and top and bottom surfaces adapted for gripping opposed vertebral endplates, wherein the front wall comprises at least one threaded throughhole,
  b) a bone screw received in the threaded throughhole, the bone screw having a threaded shaft and a proximal head, c) the inserter of FIGS. 8A-8F,
  wherein the distal tip of the inserter is received in the proximal head of the bone screw.

While this invention has been particularly shown and described with references to preferred embodiments thereof, it will be understood by those skilled in the art that various changes in form and details may be made therein without departing from the scope of the invention encompassed by the appended claims.

We claim:

1. A flexible bone screw driver comprising:
a) a proximal handle,
b) an intermediate shaft,
c) a flexible distal end portion comprising a plurality of interlocking segments portion defining a periphery and a distal tip adapted to engage a screw head, and
d) a flexible pre-bent sleeve that is configured to be placed radially over and around the plurality of interlocking segments to provide a loaded configuration,
wherein the plurality of interlocking segments portion is substantially straight in its unloaded configuration,
whereby the pre-bent sleeve pre-determines the trajectory of the tip in the loaded configuration,
wherein the sleeve substantially contacts at least one-half of the periphery of the plurality of interlocking segments portion,
wherein the sleeve is adapted to rotate about its longitudinal axis during torque transmission when the distal tip is received in a proximal head of an implanted bone screw,
wherein a distal end of the sleeve is proximal to the distal tip of the flexible distal end portion.

2. The driver of claim 1 wherein the pre-bent sleeve comprises a longitudinal slit.

3. An assembly comprising:
a) a fusion cage comprising a front wall, a pair of opposing side walls, a back wall, and top and bottom surfaces adapted for gripping opposed vertebral endplates, wherein the front wall comprises at least one threaded throughhole,
b) a bone screw received in the threaded throughhole, the bone screw having a threaded shaft and a proximal head,
c) the driver of claim 1,
wherein the distal tip of the inserter is received in the proximal head of the bone screw, wherein the first bone screw extends through the top surface of the cage.

* * * * *